US012788408B2

(12) United States Patent
Wei

(10) Patent No.: US 12,788,408 B2
(45) Date of Patent: Nov. 10, 2026

(54) TISSUE FIXATION DEVICES AND METHODS

(71) Applicant: Abbott Cardiovascular Systems Inc., Abbott Park, IL (US)

(72) Inventor: Michael F. Wei, Redwood City, CA (US)

(73) Assignee: Abbott Cardiovascular Systems Inc., Abbott Park, IL (US)

( * ) Notice: Subject to any disclaimer, the term of this patent is extended or adjusted under 35 U.S.C. 154(b) by 86 days.

(21) Appl. No.: 18/947,063

(22) Filed: Nov. 14, 2024

(65) Prior Publication Data

US 2025/0064457 A1 Feb. 27, 2025

Related U.S. Application Data

(60) Division of application No. 17/148,186, filed on Jan. 13, 2021, now Pat. No. 12,178,443, which is a (Continued)

(51) Int. Cl.
*A61B 17/122* (2006.01)
*A61B 17/08* (2006.01)
(Continued)

(52) U.S. Cl.
CPC ........ *A61B 17/1227* (2013.01); *A61B 17/083* (2013.01); *A61B 17/122* (2013.01); (Continued)

(58) Field of Classification Search
CPC .... A61B 2017/00243; A61B 2017/081; A61B 2017/083; A61B 17/08; A61B 17/122; (Continued)

(56) References Cited

U.S. PATENT DOCUMENTS 2,097,018 A 10/1937 Chamberlin
2,108,206 A 2/1938 Meeker
(Continued)

FOREIGN PATENT DOCUMENTS

CA 2509610 12/2005
CA 2296317 C 1/2009
(Continued)

OTHER PUBLICATIONS

Abe et al."De Vega's annuloplasty for acquired tricuspid disease: Early and late results in 110 patients" Ann. Thorac. Surg. (1989) 48:670-676.
(Continued)

*Primary Examiner* — Katherine H Schwiker
(74) *Attorney, Agent, or Firm* — SLEMAN & LUND LLP

(57) ABSTRACT

The present disclosure describes tissue gripping devices, systems, and methods for gripping mitral valve tissue during treatment of a mitral valve and while a tissue fixation device is implanted in the mitral valve. The tissue gripping device includes a flexible member and one or more tissue gripping members coupled to one or more arms of the flexible member. The flexible member is formed from a shape-memory material, such as nitinol, and the tissue gripping member(s) are formed from a material that is more rigid than the shape-memory material. The tissue gripping member(s) are attached to the flexible member by threading or looping suture lines around and/or through the tissue gripping member(s) and the flexible member and/or by applying a cover material to the tissue gripping device to hold the tissue gripping member(s) against the flexible member.

19 Claims, 9 Drawing Sheets

Related U.S. Application Data continuation of application No. 16/050,445, filed on Jul. 31, 2018, now Pat. No. 10,893,941, which is a continuation of application No. 14/677,294, filed on Apr. 2, 2015, now Pat. No. 10,524,912.

(51) Int. Cl.
*A61F 2/24* (2006.01)
*A61B 17/00* (2006.01)

(52) U.S. Cl.
CPC ............ *A61F 2/2454* (2013.01); *A61F 2/246* (2013.01); *A61B 2017/00243* (2013.01); *A61B 2017/00526* (2013.01); *A61B 2017/00867* (2013.01); *A61B 2017/00964* (2013.01); *A61B 2017/081* (2013.01); *A61F 2220/0016* (2013.01)

(58) Field of Classification Search
CPC ............. A61B 17/1285; A61B 17/1277; A61F 2/2454; A61F 2/246
See application file for complete search history.

(56) References Cited

U.S. PATENT DOCUMENTS 3,296,668 A 1/1967 Aiken
3,378,010 A 4/1968 Codling
3,557,780 A 1/1971 Sato
3,671,979 A 6/1972 Moulopoulos
3,675,639 A 7/1972 Cimber
3,874,338 A 4/1975 Happel
3,874,388 A 4/1975 King
4,007,743 A 2/1977 Blake
4,055,861 A 11/1977 Carpentier
4,056,854 A 11/1977 Boretos
4,064,881 A 12/1977 Meredith
4,091,815 A 5/1978 Larsen
4,112,951 A 9/1978 Hulka
4,235,238 A 11/1980 Ogiu
4,297,749 A 11/1981 Davis
4,327,736 A 5/1982 Inoue
4,340,091 A 7/1982 Skelton
4,425,908 A 1/1984 Simon
4,458,682 A 7/1984 Cerwin
4,484,579 A 11/1984 Meno
4,487,205 A 12/1984 Di Giovanni
4,498,476 A 2/1985 Cerwin
4,510,934 A 4/1985 Batra
4,531,522 A 7/1985 Bedi
4,578,061 A 3/1986 Lemelson
4,641,366 A 2/1987 Yokoyama
4,657,024 A 4/1987 Coneys
4,686,965 A 8/1987 Bonnet
4,693,248 A 9/1987 Failla
4,716,886 A 1/1988 Schulman
4,777,951 A 10/1988 Cribier
4,795,458 A 1/1989 Regan
4,809,695 A 3/1989 Gwathmey
4,917,089 A 4/1990 Sideris
4,930,674 A 6/1990 Barak
4,944,295 A 7/1990 Gwathmey
4,969,890 A 11/1990 Sugita
4,994,077 A 2/1991 Dobben
5,002,562 A 3/1991 Oberlander
5,015,249 A 5/1991 Nakao
5,019,096 A 5/1991 Fox, Jr.
5,042,707 A 8/1991 Taheri
5,047,041 A 9/1991 Samuels
5,049,153 A 9/1991 Nakao
5,061,277 A 10/1991 Carpentier
5,069,679 A 12/1991 Taheri
5,098,440 A 3/1992 Hillstead
5,108,368 A 4/1992 Hammerslag
5,125,758 A 6/1992 Dewan
5,125,895 A 6/1992 Buchbinder
5,147,370 A 9/1992 Mcnamara
5,171,252 A 12/1992 Friedland
5,171,259 A 12/1992 Inoue
5,190,554 A 3/1993 Coddington, III
5,195,968 A 3/1993 Lundquist
5,209,756 A 5/1993 Seedhom
5,222,963 A 6/1993 Brinkerhoff
5,226,429 A 7/1993 Kuzmak
5,226,911 A 7/1993 Chee
5,234,437 A 8/1993 Sepetka
5,242,456 A 9/1993 Nash
5,250,071 A 10/1993 Palermo
5,251,611 A 10/1993 Zehel
5,254,130 A 10/1993 Poncet
5,261,916 A 11/1993 Engelson
5,271,381 A 12/1993 Ailinger
5,271,544 A 12/1993 Fox
5,275,578 A 1/1994 Adams
5,282,845 A 2/1994 Bush
5,304,131 A 4/1994 Paskar
5,306,283 A 4/1994 Conners
5,306,286 A 4/1994 Stack
5,312,415 A 5/1994 Palermo
5,314,424 A 5/1994 Nicholas
5,318,525 A 6/1994 West
5,320,632 A 6/1994 Heidmueller
5,325,845 A 7/1994 Adair
5,327,905 A 7/1994 Avitall
5,330,442 A 7/1994 Green
5,330,501 A 7/1994 Tovey
5,332,402 A 7/1994 Teitelbaum
5,334,217 A 8/1994 Das
5,342,393 A 8/1994 Stack
5,350,397 A 9/1994 Palermo
5,350,399 A 9/1994 Erlebacher
5,359,994 A 11/1994 Krauter
5,363,861 A 11/1994 Edwards
5,368,564 A 11/1994 Savage
5,368,601 A 11/1994 Sauer
5,383,886 A 1/1995 Kensey
5,389,077 A 2/1995 Melinyshyn
5,391,182 A 2/1995 Chin
5,403,312 A 4/1995 Yates
5,403,326 A 4/1995 Harrison
5,411,552 A 5/1995 Andersen
5,413,584 A 5/1995 Schulze
5,417,699 A 5/1995 Klein
5,417,700 A 5/1995 Egan
5,423,857 A 6/1995 Rosenman
5,423,858 A 6/1995 Bolanos
5,423,882 A 6/1995 Jackman
5,425,744 A 6/1995 Fagan
5,431,666 A 7/1995 Sauer
5,437,551 A 8/1995 Chalifoux
5,437,681 A 8/1995 Meade
5,447,966 A 9/1995 Hermes
5,450,860 A 9/1995 O'Connor
5,452,837 A 9/1995 Williamson, IV
5,456,400 A 10/1995 Shichman
5,456,674 A 10/1995 Bos
5,456,684 A 10/1995 Schmidt
5,462,527 A 10/1995 Stevens-Wright
5,472,044 A 12/1995 Hall
5,476,470 A 12/1995 Fitzgibbons, Jr.
5,477,856 A 12/1995 Lundquist
5,478,309 A 12/1995 Sweezer
5,478,353 A 12/1995 Yoon
5,487,746 A 1/1996 Yu
5,496,332 A 3/1996 Sierra
5,507,725 A 4/1996 Savage
5,507,755 A 4/1996 Gresl
5,507,757 A 4/1996 Sauer
5,520,701 A 5/1996 Lerch
5,522,873 A 6/1996 Jackman
5,527,313 A 6/1996 Scott
5,527,321 A 6/1996 Hinchliffe
5,527,322 A 6/1996 Klein
5,536,251 A 7/1996 Evard

(56) References Cited

U.S. PATENT DOCUMENTS 5,540,705 A 7/1996 Meade
5,542,949 A 8/1996 Yoon
5,554,185 A 9/1996 Block
5,562,678 A 10/1996 Booker
5,569,274 A 10/1996 Rapacki
5,571,085 A 11/1996 Accisano, III
5,571,137 A 11/1996 Marlow
5,571,215 A 11/1996 Sterman
5,575,802 A 11/1996 Mcquilkin
5,582,611 A 12/1996 Tsuruta
5,593,424 A 1/1997 Northrup, III
5,593,435 A 1/1997 Carpentier
5,601,224 A 2/1997 Bishop
5,601,574 A 2/1997 Stefanchik
5,607,462 A 3/1997 Imran
5,607,471 A 3/1997 Seguin
5,609,598 A 3/1997 Laufer
5,611,794 A 3/1997 Sauer
5,618,306 A 4/1997 Roth
5,620,452 A 4/1997 Yoon
5,620,461 A 4/1997 Muijs Van De Moer
5,626,588 A 5/1997 Sauer
5,634,932 A 6/1997 Schmidt
5,636,634 A 6/1997 Kordis
5,639,277 A 6/1997 Mariant
5,640,955 A 6/1997 Ockuly
5,649,937 A 7/1997 Bito
5,662,681 A 9/1997 Nash
5,669,917 A 9/1997 Sauer
5,690,671 A 11/1997 McGurk
5,695,504 A 12/1997 Gifford, III
5,695,505 A 12/1997 Yoon
5,702,825 A 12/1997 Keita
5,706,824 A 1/1998 Whittier
5,709,707 A 1/1998 Lock
5,713,910 A 2/1998 Gordon
5,713,911 A 2/1998 Racenet
5,715,817 A 2/1998 Stevens-Wright
5,716,367 A 2/1998 Koike
5,716,417 A 2/1998 Girard
5,718,725 A 2/1998 Sterman
5,719,725 A 2/1998 Nakao
5,722,421 A 3/1998 Francese
5,725,542 A 3/1998 Yoon
5,725,556 A 3/1998 Moser
5,738,649 A 4/1998 Macoviak
5,741,280 A 4/1998 Fleenor
5,741,297 A 4/1998 Simon
5,749,828 A 5/1998 Yeung
5,755,778 A 5/1998 Kleshinski
5,759,193 A 6/1998 Burbank
5,769,812 A 6/1998 Stevens
5,769,863 A 6/1998 Garrison
5,772,578 A 6/1998 Heimberger
5,782,239 A 7/1998 Webster, Jr.
5,782,845 A 7/1998 Shewchuk
5,797,927 A 8/1998 Yoon
5,797,960 A 8/1998 Stevens
5,810,847 A 9/1998 Laufer
5,810,849 A 9/1998 Kontos
5,810,853 A 9/1998 Yoon
5,810,876 A 9/1998 Kelleher
5,814,029 A 9/1998 Hassett
5,814,097 A 9/1998 Sterman
5,820,592 A 10/1998 Hammerslag
5,820,631 A 10/1998 Nobles
5,823,955 A 10/1998 Kuck
5,823,956 A 10/1998 Roth
5,824,065 A 10/1998 Gross
5,827,237 A 10/1998 Macoviak
5,829,447 A 11/1998 Stevens
5,833,671 A 11/1998 Macoviak
5,836,955 A 11/1998 Buelna
5,840,081 A 11/1998 Andersen
5,843,031 A 12/1998 Hermann
5,843,178 A 12/1998 Vanney
5,849,019 A 12/1998 Yoon
5,853,422 A 12/1998 Huebsch
5,855,271 A 1/1999 Eubanks
5,855,590 A 1/1999 Malecki
5,855,601 A 1/1999 Bessler
5,855,614 A 1/1999 Stevens
5,860,990 A 1/1999 Nobles
5,861,003 A 1/1999 Latson
5,868,733 A 2/1999 Ockuly
5,876,399 A 3/1999 Chia
5,879,307 A 3/1999 Chio
5,885,258 A 3/1999 Sachdeva
5,885,271 A 3/1999 Hamilton
5,891,160 A 4/1999 Williamson, IV
5,916,147 A 6/1999 Boury
5,928,224 A 7/1999 Laufer
5,944,733 A 8/1999 Engelson
5,947,363 A 9/1999 Bolduc
5,954,732 A 9/1999 Hart
5,957,949 A 9/1999 Leonhardt
5,972,020 A 10/1999 Carpentier
5,972,030 A 10/1999 Garrison
5,976,159 A 11/1999 Bolduc
5,980,455 A 11/1999 Daniel
5,989,284 A 11/1999 Laufer
6,007,552 A 12/1999 Fogarty
6,015,417 A 1/2000 Reynolds, Jr.
6,017,358 A 1/2000 Yoon
6,019,722 A 2/2000 Spence
6,022,360 A 2/2000 Reimels
6,033,378 A 3/2000 Lundquist
6,036,699 A 3/2000 Andreas
6,048,351 A 4/2000 Gordon
6,056,769 A 5/2000 Epstein
6,059,757 A 5/2000 Macoviak
6,060,628 A 5/2000 Aoyama
6,060,629 A 5/2000 Pham
6,063,106 A 5/2000 Gibson
6,066,146 A 5/2000 Carroll
6,068,628 A 5/2000 Fanton
6,068,629 A 5/2000 Haissaguerre
6,077,214 A 6/2000 Mortier
6,079,414 A 6/2000 Roth
6,086,600 A 7/2000 Kortenbach
6,088,889 A 7/2000 Luther
6,099,505 A 8/2000 Ryan
6,099,553 A 8/2000 Hart
6,110,145 A 8/2000 Macoviak
6,117,144 A 9/2000 Nobles
6,117,159 A 9/2000 Huebsch
6,120,496 A 9/2000 Whayne
6,123,699 A 9/2000 Webster, Jr.
6,126,658 A 10/2000 Baker
6,132,447 A 10/2000 Dorsey
6,136,010 A 10/2000 Modesitt
6,143,024 A 11/2000 Campbell
6,149,658 A 11/2000 Gardiner
6,156,055 A 12/2000 Ravenscroft
6,159,240 A 12/2000 Sparer
6,162,233 A 12/2000 Williamson, IV
6,165,164 A 12/2000 Hill
6,165,183 A 12/2000 Kuehn
6,165,204 A 12/2000 Levinson
6,168,614 B1 1/2001 Andersen
6,171,320 B1 1/2001 Monassevitch
6,182,664 B1 2/2001 Cosgrove
6,187,003 B1 2/2001 Buysse
6,190,408 B1 2/2001 Melvin
6,193,734 B1 2/2001 Bolduc
6,200,315 B1 3/2001 Gaiser
6,203,531 B1 3/2001 Ockuly
6,203,553 B1 3/2001 Robertson
6,206,893 B1 3/2001 Klein
6,206,907 B1 3/2001 Marino
6,210,419 B1 4/2001 Mayenberger
6,210,432 B1 4/2001 Solem
6,217,528 B1 4/2001 Koblish
6,245,079 B1 6/2001 Nobles

(56) References Cited

U.S. PATENT DOCUMENTS

| | | | |
|---|---|---|---|
| 6,267,746 | B1 | 7/2001 | Bumbalough |
| 6,267,781 | B1 | 7/2001 | Tu |
| 6,269,819 | B1 | 8/2001 | Oz |
| 6,277,555 | B1 | 8/2001 | Duran |
| 6,283,127 | B1 | 9/2001 | Sterman |
| 6,283,962 | B1 | 9/2001 | Tu |
| 6,290,674 | B1 | 9/2001 | Roue |
| 6,299,637 | B1 | 10/2001 | Shaolian |
| 6,306,133 | B1 | 10/2001 | Tu |
| 6,312,447 | B1 | 11/2001 | Grimes |
| 6,319,250 | B1 | 11/2001 | Falwell |
| 6,322,559 | B1 | 11/2001 | Daulton |
| 6,332,880 | B1 | 12/2001 | Yang |
| 6,332,893 | B1 | 12/2001 | Mortier |
| 6,346,074 | B1 | 2/2002 | Roth |
| 6,352,708 | B1 | 3/2002 | Duran |
| 6,355,030 | B1 | 3/2002 | Aldrich |
| 6,358,277 | B1 | 3/2002 | Duran |
| 6,368,326 | B1 | 4/2002 | Dakin |
| 6,387,104 | B1 | 5/2002 | Pugsley, Jr. |
| 6,402,780 | B2 | 6/2002 | Williamson, IV |
| 6,402,781 | B1 | 6/2002 | Langberg |
| 6,406,420 | B1 | 6/2002 | Mccarthy |
| 6,419,669 | B1 | 7/2002 | Frazier |
| 6,419,696 | B1 | 7/2002 | Ortiz |
| 6,461,366 | B1 | 10/2002 | Seguin |
| 6,464,707 | B1 | 10/2002 | Bjerken |
| 6,482,224 | B1 | 11/2002 | Michler |
| 6,485,489 | B2 | 11/2002 | Teirstein |
| 6,508,828 | B1 | 1/2003 | Akerfeldt |
| 6,533,796 | B1 | 3/2003 | Sauer |
| 6,537,314 | B2 | 3/2003 | Langberg |
| 6,540,755 | B2 | 4/2003 | Ockuly |
| 6,544,215 | B1 | 4/2003 | Bencini |
| 6,551,303 | B1 | 4/2003 | Van Tassel |
| 6,551,331 | B2 | 4/2003 | Nobles |
| 6,562,037 | B2 | 5/2003 | Paton |
| 6,562,052 | B2 | 5/2003 | Nobles |
| 6,575,971 | B2 | 6/2003 | Hauck |
| 6,585,761 | B2 | 7/2003 | Taheri |
| 6,599,311 | B1 | 7/2003 | Biggs |
| 6,616,684 | B1 | 9/2003 | Vidlund |
| 6,619,291 | B2 | 9/2003 | Hlavka |
| 6,626,899 | B2 | 9/2003 | Houser |
| 6,626,930 | B1 | 9/2003 | Allen |
| 6,629,534 | B1 | 10/2003 | St Goar |
| 6,641,592 | B1 | 11/2003 | Sauer |
| 6,656,221 | B2 | 12/2003 | Taylor |
| 6,669,687 | B1 | 12/2003 | Saadat |
| 6,685,648 | B2 | 2/2004 | Flaherty |
| 6,689,164 | B1 | 2/2004 | Seguin |
| 6,695,866 | B1 | 2/2004 | Kuehn |
| 6,701,929 | B2 | 3/2004 | Hussein |
| 6,702,825 | B2 | 3/2004 | Frazier |
| 6,702,826 | B2 | 3/2004 | Liddicoat |
| 6,709,382 | B1 | 3/2004 | Horner |
| 6,709,456 | B2 | 3/2004 | Langberg |
| 6,718,985 | B2 | 4/2004 | Hlavka |
| 6,719,767 | B1 | 4/2004 | Kimblad |
| 6,723,038 | B1 | 4/2004 | Schroeder |
| 6,726,716 | B2 | 4/2004 | Marquez |
| 6,740,107 | B2 | 5/2004 | Loeb |
| 6,746,471 | B2 | 6/2004 | Mortier |
| 6,752,813 | B2 | 6/2004 | Goldfarb |
| 6,755,777 | B2 | 6/2004 | Schweich, Jr. |
| 6,764,510 | B2 | 7/2004 | Vidlund |
| 6,767,349 | B2 | 7/2004 | Ouchi |
| 6,770,083 | B2 | 8/2004 | Seguin |
| 6,797,001 | B2 | 9/2004 | Mathis |
| 6,797,002 | B2 | 9/2004 | Spence |
| 6,837,867 | B2 | 1/2005 | Kortelling |
| 6,855,137 | B2 | 2/2005 | Bon |
| 6,860,179 | B2 | 3/2005 | Hopper |
| 6,875,224 | B2 | 4/2005 | Grimes |
| 6,908,481 | B2 | 6/2005 | Cribier |
| 6,926,715 | B1 | 8/2005 | Hauck |
| 6,926,730 | B1 | 8/2005 | Nguyen |
| 6,945,978 | B1 | 9/2005 | Hyde |
| 6,949,122 | B2 | 9/2005 | Adams |
| 6,966,914 | B2 | 11/2005 | Abe |
| 6,986,775 | B2 | 1/2006 | Morales |
| 7,004,970 | B2 | 2/2006 | Cauthen III |
| 7,011,669 | B2 | 3/2006 | Kimblad |
| 7,048,754 | B2 | 5/2006 | Martin |
| 7,101,395 | B2 | 9/2006 | Tremulis |
| 7,112,207 | B2 | 9/2006 | Allen |
| 7,226,467 | B2 | 6/2007 | Lucatero |
| 7,288,097 | B2 | 10/2007 | Seguin |
| 7,381,210 | B2 | 6/2008 | Zarbatany |
| 7,464,712 | B2 | 12/2008 | Oz |
| 7,497,822 | B1 | 3/2009 | Kugler |
| 7,513,908 | B2 | 4/2009 | Lattouf |
| 7,533,790 | B1 | 5/2009 | Knodel |
| 7,563,267 | B2 | 7/2009 | Goldfarb |
| 7,563,273 | B2 | 7/2009 | Goldfarb |
| 7,569,062 | B1 | 8/2009 | Kuehn |
| 7,604,646 | B2 | 10/2009 | Goldfarb |
| 7,608,091 | B2 | 10/2009 | Goldfarb |
| 7,635,329 | B2 | 12/2009 | Goldfarb |
| 7,651,502 | B2 | 1/2010 | Jackson |
| 7,655,015 | B2 | 2/2010 | Goldfarb |
| 7,655,040 | B2 | 2/2010 | Douk |
| 7,666,204 | B2 | 2/2010 | Thornton |
| 7,704,269 | B2 | 4/2010 | St Goar |
| 7,798,953 | B1 | 9/2010 | Wilk |
| 7,811,296 | B2 | 10/2010 | Goldfarb |
| 7,914,544 | B2 | 3/2011 | Nguyen |
| 7,972,323 | B1 | 7/2011 | Bencini |
| 7,972,330 | B2 | 7/2011 | Alejandro |
| 8,029,565 | B2 | 10/2011 | Lattouf |
| 8,052,592 | B2 | 11/2011 | Goldfarb |
| 8,062,313 | B2 | 11/2011 | Kimblad |
| 8,118,822 | B2 | 2/2012 | Schaller |
| 8,216,256 | B2 | 7/2012 | Raschdorf, Jr. |
| 8,348,963 | B2 | 1/2013 | Wilson |
| 8,940,001 | B2 | 1/2015 | Catanese, III |
| 9,572,666 | B2 | 2/2017 | Basude |
| 10,893,941 | B2 | 1/2021 | Wei |
| 2001/0004715 | A1 | 6/2001 | Duran |
| 2001/0005787 | A1 | 6/2001 | Oz |
| 2001/0010005 | A1 | 7/2001 | Kammerer |
| 2001/0018611 | A1 | 8/2001 | Solem |
| 2001/0022872 | A1 | 9/2001 | Marui |
| 2001/0027322 | A1 | 10/2001 | Bowman |
| 2001/0037084 | A1 | 11/2001 | Nardeo |
| 2001/0039411 | A1 | 11/2001 | Johansson |
| 2001/0044568 | A1 | 11/2001 | Langberg |
| 2002/0013571 | A1 | 1/2002 | Goldfarb |
| 2002/0022848 | A1 | 2/2002 | Garrison |
| 2002/0026233 | A1 | 2/2002 | Shaknovich |
| 2002/0035361 | A1 | 3/2002 | Houser |
| 2002/0035381 | A1 | 3/2002 | Bardy |
| 2002/0042651 | A1 | 4/2002 | Liddicoat |
| 2002/0055767 | A1 | 5/2002 | Forde |
| 2002/0055774 | A1 | 5/2002 | Liddicoat |
| 2002/0055775 | A1 | 5/2002 | Carpentier |
| 2002/0058910 | A1 | 5/2002 | Hermann |
| 2002/0058995 | A1 | 5/2002 | Stevens |
| 2002/0077687 | A1 | 6/2002 | Ahn |
| 2002/0082621 | A1 | 6/2002 | Schurr |
| 2002/0087148 | A1 | 7/2002 | Brock |
| 2002/0087169 | A1 | 7/2002 | Brock |
| 2002/0087173 | A1 | 7/2002 | Alferness |
| 2002/0103532 | A1 | 8/2002 | Langberg |
| 2002/0107534 | A1 | 8/2002 | Schaefer |
| 2002/0133178 | A1 | 9/2002 | Muramatsu |
| 2002/0147456 | A1 | 10/2002 | Diduch |
| 2002/0156526 | A1 | 10/2002 | Hlavka |
| 2002/0158528 | A1 | 10/2002 | Tsuzaki |
| 2002/0161378 | A1 | 10/2002 | Downing |
| 2002/0169360 | A1 | 11/2002 | Taylor |
| 2002/0183766 | A1 | 12/2002 | Seguin |
| 2002/0183787 | A1 | 12/2002 | Wahr |
| 2002/0183835 | A1 | 12/2002 | Taylor |

(56) References Cited

U.S. PATENT DOCUMENTS

| | | | |
|---|---|---|---|
| 2003/0005797 | A1 | 1/2003 | Hopper |
| 2003/0018358 | A1 | 1/2003 | Saadat |
| 2003/0045778 | A1 | 3/2003 | Ohline |
| 2003/0050693 | A1 | 3/2003 | Quijano |
| 2003/0069570 | A1 | 4/2003 | Witzel |
| 2003/0069593 | A1 | 4/2003 | Tremulis |
| 2003/0069636 | A1 | 4/2003 | Solem |
| 2003/0074012 | A1 | 4/2003 | Nguyen |
| 2003/0078654 | A1 | 4/2003 | Taylor |
| 2003/0083742 | A1 | 5/2003 | Spence |
| 2003/0105519 | A1 | 6/2003 | Fasol |
| 2003/0105520 | A1 | 6/2003 | Alferness |
| 2003/0120340 | A1 | 6/2003 | Liska |
| 2003/0120341 | A1 | 6/2003 | Shennib |
| 2003/0130669 | A1 | 7/2003 | Damarati |
| 2003/0130694 | A1 | 7/2003 | Bojarski |
| 2003/0130730 | A1 | 7/2003 | Cohn |
| 2003/0144697 | A1 | 7/2003 | Mathis |
| 2003/0167071 | A1 | 9/2003 | Martin |
| 2003/0171776 | A1 | 9/2003 | Adams |
| 2003/0187467 | A1 | 10/2003 | Schreck |
| 2003/0195562 | A1 | 10/2003 | Collier |
| 2003/0208231 | A1 | 11/2003 | Williamson |
| 2003/0225423 | A1 | 12/2003 | Huitema |
| 2003/0229395 | A1 | 12/2003 | Cox |
| 2003/0233038 | A1 | 12/2003 | Hassett |
| 2004/0002719 | A1 | 1/2004 | Oz |
| 2004/0003819 | A1 | 1/2004 | St Goar |
| 2004/0019377 | A1 | 1/2004 | Taylor |
| 2004/0019378 | A1 | 1/2004 | Hlavka |
| 2004/0024414 | A1 | 2/2004 | Downing |
| 2004/0030382 | A1 | 2/2004 | St Goar |
| 2004/0034365 | A1 | 2/2004 | Lentz |
| 2004/0039442 | A1 | 2/2004 | St Goar |
| 2004/0039443 | A1 | 2/2004 | Solem |
| 2004/0044350 | A1 | 3/2004 | Martin |
| 2004/0044365 | A1 | 3/2004 | Bachman |
| 2004/0049207 | A1 | 3/2004 | Goldfarb |
| 2004/0049211 | A1 | 3/2004 | Tremulis |
| 2004/0073302 | A1 | 4/2004 | Rourke |
| 2004/0078053 | A1 | 4/2004 | Berg |
| 2004/0087975 | A1 | 5/2004 | Lucatero |
| 2004/0088047 | A1 | 5/2004 | Spence |
| 2004/0092962 | A1 | 5/2004 | Thornton |
| 2004/0093023 | A1 | 5/2004 | Allen |
| 2004/0097878 | A1 | 5/2004 | Anderson |
| 2004/0097979 | A1 | 5/2004 | Svanidze |
| 2004/0106989 | A1 | 6/2004 | Wilson |
| 2004/0111099 | A1 | 6/2004 | Nguyen |
| 2004/0122448 | A1 | 6/2004 | Levine |
| 2004/0127981 | A1 | 7/2004 | Rahdert |
| 2004/0127982 | A1 | 7/2004 | Machold |
| 2004/0127983 | A1 | 7/2004 | Mortier |
| 2004/0133062 | A1 | 7/2004 | Pai |
| 2004/0133063 | A1 | 7/2004 | Mccarthy |
| 2004/0133082 | A1 | 7/2004 | Abraham-Fuchs |
| 2004/0133192 | A1 | 7/2004 | Houser |
| 2004/0133220 | A1 | 7/2004 | Lashinski |
| 2004/0133240 | A1 | 7/2004 | Adams |
| 2004/0133273 | A1 | 7/2004 | Cox |
| 2004/0138744 | A1 | 7/2004 | Lashinski |
| 2004/0138745 | A1 | 7/2004 | Macoviak |
| 2004/0148021 | A1 | 7/2004 | Cartledge |
| 2004/0152847 | A1 | 8/2004 | Emri |
| 2004/0152947 | A1 | 8/2004 | Schroeder |
| 2004/0153144 | A1 | 8/2004 | Seguin |
| 2004/0158123 | A1 | 8/2004 | Jayaraman |
| 2004/0162610 | A1 | 8/2004 | Liska |
| 2004/0167539 | A1 | 8/2004 | Kuehn |
| 2004/0186486 | A1 | 9/2004 | Roue |
| 2004/0186566 | A1 | 9/2004 | Hindrichs |
| 2004/0193191 | A1 | 9/2004 | Starksen |
| 2004/0215339 | A1 | 10/2004 | Drasler |
| 2004/0220593 | A1 | 11/2004 | Greenhalgh |
| 2004/0220657 | A1 | 11/2004 | Nieminen |
| 2004/0225300 | A1 | 11/2004 | Goldfarb |
| 2004/0236354 | A1 | 11/2004 | Seguin |
| 2004/0243229 | A1 | 12/2004 | Mdlund |
| 2004/0249452 | A1 | 12/2004 | Adams |
| 2004/0249453 | A1 | 12/2004 | Cartledge |
| 2004/0260393 | A1 | 12/2004 | Rahdert |
| 2005/0004583 | A1 | 1/2005 | Oz |
| 2005/0004665 | A1 | 1/2005 | Aklog |
| 2005/0004668 | A1 | 1/2005 | Aklog |
| 2005/0021056 | A1 | 1/2005 | St Goar |
| 2005/0021057 | A1 | 1/2005 | St Goar |
| 2005/0021058 | A1 | 1/2005 | Negro |
| 2005/0033446 | A1 | 2/2005 | Deem |
| 2005/0038508 | A1 | 2/2005 | Gabbay |
| 2005/0049698 | A1 | 3/2005 | Bolling |
| 2005/0055089 | A1 | 3/2005 | Macoviak |
| 2005/0059351 | A1 | 3/2005 | Cauwels |
| 2005/0149014 | A1 | 7/2005 | Hauck |
| 2005/0159810 | A1 | 7/2005 | Filsoufi |
| 2005/0197694 | A1 | 9/2005 | Pai |
| 2005/0197695 | A1 | 9/2005 | Stacchino |
| 2005/0216039 | A1 | 9/2005 | Lederman |
| 2005/0228422 | A1 | 10/2005 | Machold |
| 2005/0228495 | A1 | 10/2005 | Macoviak |
| 2005/0251001 | A1 | 11/2005 | Hassett |
| 2005/0267493 | A1 | 12/2005 | Schreck |
| 2005/0273160 | A1 | 12/2005 | Lashinski |
| 2005/0287493 | A1 | 12/2005 | Novak |
| 2006/0004247 | A1 | 1/2006 | Kute |
| 2006/0015003 | A1 | 1/2006 | Moaddes |
| 2006/0020275 | A1 | 1/2006 | Goldfarb |
| 2006/0030866 | A1 | 2/2006 | Schreck |
| 2006/0030867 | A1 | 2/2006 | Zadno |
| 2006/0030885 | A1 | 2/2006 | Hyde |
| 2006/0058871 | A1 | 3/2006 | Zakay |
| 2006/0064115 | A1 | 3/2006 | Allen |
| 2006/0064116 | A1 | 3/2006 | Allen |
| 2006/0064118 | A1 | 3/2006 | Kimblad |
| 2006/0089671 | A1 | 4/2006 | Goldfarb |
| 2006/0089711 | A1 | 4/2006 | Dolan |
| 2006/0135993 | A1 | 6/2006 | Seguin |
| 2006/0184203 | A1 | 8/2006 | Martin |
| 2006/0190036 | A1 | 8/2006 | Wendel |
| 2006/0195012 | A1 | 8/2006 | Mortier |
| 2006/0229708 | A1 | 10/2006 | Powell |
| 2006/0252984 | A1 | 11/2006 | Rahdert |
| 2006/0293701 | A1 | 12/2006 | Ainsworth |
| 2007/0038293 | A1 | 2/2007 | St Goar |
| 2007/0100356 | A1 | 5/2007 | Lucatero |
| 2007/0118155 | A1 | 5/2007 | Goldfarb |
| 2007/0129737 | A1 | 6/2007 | Goldfarb |
| 2007/0162125 | A1 | 7/2007 | LeBeau |
| 2007/0197858 | A1 | 8/2007 | Goldfarb |
| 2007/0198082 | A1 | 8/2007 | Kapadia |
| 2007/0213747 | A1 | 9/2007 | Monassevitch |
| 2008/0039935 | A1 | 2/2008 | Buch |
| 2008/0051703 | A1 | 2/2008 | Thornton |
| 2008/0051807 | A1 | 2/2008 | St Goar |
| 2008/0097489 | A1 | 4/2008 | Goldfarb |
| 2008/0167714 | A1 | 7/2008 | St Goar |
| 2008/0183194 | A1 | 7/2008 | Goldfarb |
| 2009/0156995 | A1 | 6/2009 | Martin |
| 2009/0163934 | A1 | 6/2009 | Raschdorf, Jr. |
| 2009/0177266 | A1 | 7/2009 | Powell |
| 2009/0182419 | A1 | 7/2009 | Bolling |
| 2009/0198322 | A1 | 8/2009 | Deem |
| 2009/0270858 | A1 | 10/2009 | Hauck |
| 2009/0326567 | A1 | 12/2009 | Goldfarb |
| 2010/0016899 | A1 | 1/2010 | Gelfand |
| 2010/0016958 | A1 | 1/2010 | St Goar |
| 2010/0022823 | A1 | 1/2010 | Goldfarb |
| 2010/0152753 | A1 | 6/2010 | Menn |
| 2010/0324585 | A1 | 12/2010 | Miles |
| 2012/0296349 | A1 | 11/2012 | Smith |
| 2013/0035759 | A1 | 2/2013 | Gross |
| 2013/0066341 | A1 | 3/2013 | Ketai |
| 2013/0066342 | A1 | 3/2013 | Dell |
| 2013/0073029 | A1 | 3/2013 | Shaw |
| 2013/0138121 | A1 | 5/2013 | Allen |

(56) References Cited

U.S. PATENT DOCUMENTS

| | | | |
|---|---|---|---|
| 2013/0253642 | A1 | 9/2013 | Brecker |
| 2013/0261638 | A1 | 10/2013 | Diamant |
| 2014/0066693 | A1 | 3/2014 | Goldfarb |
| 2014/0067054 | A1 | 3/2014 | Chau |
| 2014/0249553 | A1 | 9/2014 | Kimura |
| 2014/0309670 | A1 | 10/2014 | Bakos |
| 2015/0005809 | A1 | 1/2015 | Ayres |
| 2015/0073473 | A1 | 3/2015 | Broom |
| 2015/0223793 | A1 | 8/2015 | Goldfarb |
| 2015/0257877 | A1 | 9/2015 | Hernandez |
| 2016/0174979 | A1 | 6/2016 | Wei |
| 2016/0287387 | A1 | 10/2016 | Wei |
| 2017/0020521 | A1 | 1/2017 | Krone |
| 2018/0146966 | A1 | 5/2018 | Hernández |
| 2018/0161159 | A1 | 6/2018 | Lee |

FOREIGN PATENT DOCUMENTS

| | | | |
|---|---|---|---|
| CN | 1142351 | A | 2/1997 |
| CN | 1436060 | | 8/2003 |
| CN | 102065780 | | 5/2011 |
| CN | 102764146 | | 11/2012 |
| CN | 102860850 | | 1/2013 |
| CN | 103037778 | | 4/2013 |
| CN | 104023654 | | 9/2014 |
| DE | 10116168 | A1 | 11/2001 |
| EP | 0179562 | B1 | 7/1989 |
| EP | 0589306 | | 3/1994 |
| EP | 0684012 | A2 | 11/1995 |
| EP | 0727239 | A2 | 8/1996 |
| EP | 0782836 | A1 | 7/1997 |
| EP | 0558031 | B1 | 4/1999 |
| EP | 1199037 | A2 | 4/2002 |
| EP | 1230899 | A1 | 8/2002 |
| EP | 1383448 | A2 | 1/2004 |
| EP | 1674040 | A2 | 6/2006 |
| FR | 2768324 | A1 | 3/1999 |
| GB | 1598111 | A | 9/1981 |
| GB | 2151142 | A | 7/1985 |
| JP | H09192137 | | 7/1997 |
| JP | 09253030 | A | 9/1997 |
| JP | 11089937 | A | 4/1999 |
| JP | 2000283130 | A | 10/2000 |
| JP | 2002540878 | A | 12/2002 |
| JP | 2006528911 | A | 12/2006 |
| JP | 2015502548 | A | 1/2015 |
| JP | 5985653 | B2 | 9/2016 |
| SU | 1412751 | | 7/1988 |
| WO | 8100668 | A1 | 3/1981 |
| WO | 9101689 | A1 | 2/1991 |
| WO | 9118881 | A1 | 12/1991 |
| WO | 9212690 | A1 | 8/1992 |
| WO | 9418881 | A1 | 9/1994 |
| WO | 94018893 | A1 | 9/1994 |
| WO | 9511620 | A2 | 5/1995 |
| WO | 9515715 | A1 | 6/1995 |
| WO | 9614032 | A1 | 5/1996 |
| WO | 9620655 | A1 | 7/1996 |
| WO | 9622735 | A1 | 8/1996 |
| WO | 9630072 | A1 | 10/1996 |
| WO | 9632882 | A1 | 10/1996 |
| WO | 9718746 | A2 | 5/1997 |
| WO | 9725927 | A1 | 7/1997 |
| WO | 9726034 | A1 | 7/1997 |
| WO | 1997026034 | A1 | 7/1997 |
| WO | 9727807 | A1 | 8/1997 |
| WO | 9738748 | A2 | 10/1997 |
| WO | 9739688 | A2 | 10/1997 |
| WO | 9748436 | A2 | 12/1997 |
| WO | 9807375 | A1 | 2/1998 |
| WO | 9824372 | A1 | 6/1998 |
| WO | 9830153 | A1 | 7/1998 |
| WO | 9832382 | A1 | 7/1998 |
| WO | 9835638 | A1 | 8/1998 |
| WO | 9900059 | A1 | 1/1999 |
| WO | 9901377 | A1 | 1/1999 |
| WO | 9907354 | A2 | 2/1999 |
| WO | 9913777 | A1 | 3/1999 |
| WO | 9915223 | A1 | 4/1999 |
| WO | 9945853 | A1 | 9/1999 |
| WO | 9966967 | A1 | 12/1999 |
| WO | 0002489 | A1 | 1/2000 |
| WO | 0003651 | A1 | 1/2000 |
| WO | 0003759 | A2 | 1/2000 |
| WO | 0012168 | A1 | 3/2000 |
| WO | 0044313 | A1 | 8/2000 |
| WO | 0059382 | A1 | 10/2000 |
| WO | 0060995 | A2 | 10/2000 |
| WO | 0100111 | A1 | 1/2001 |
| WO | 0100114 | A1 | 1/2001 |
| WO | 0103651 | A2 | 1/2001 |
| WO | 0126557 | A1 | 4/2001 |
| WO | 0126586 | A1 | 4/2001 |
| WO | 0126587 | A1 | 4/2001 |
| WO | 0126588 | A2 | 4/2001 |
| WO | 0126703 | A1 | 4/2001 |
| WO | 0128432 | A1 | 4/2001 |
| WO | 0128455 | A1 | 4/2001 |
| WO | 0135832 | A2 | 5/2001 |
| WO | 0147438 | A1 | 7/2001 |
| WO | 0149213 | A2 | 7/2001 |
| WO | 0150985 | A1 | 7/2001 |
| WO | 0154618 | A1 | 8/2001 |
| WO | 0156512 | A1 | 8/2001 |
| WO | 0166001 | A2 | 9/2001 |
| WO | 0170320 | A1 | 9/2001 |
| WO | 0189440 | A2 | 11/2001 |
| WO | 0195831 | A2 | 12/2001 |
| WO | 0195832 | A2 | 12/2001 |
| WO | 0197741 | A2 | 12/2001 |
| WO | 0200099 | A2 | 1/2002 |
| WO | 0201999 | A2 | 1/2002 |
| WO | 0203892 | A1 | 1/2002 |
| WO | 2002034167 | A2 | 5/2002 |
| WO | 02060352 | A1 | 8/2002 |
| WO | 02062263 | A2 | 8/2002 |
| WO | 02062270 | A1 | 8/2002 |
| WO | 02062408 | A2 | 8/2002 |
| WO | 03001893 | A2 | 1/2003 |
| WO | 03003930 | A1 | 1/2003 |
| WO | 03020179 | A1 | 3/2003 |
| WO | 03028558 | A2 | 4/2003 |
| WO | 03037171 | A2 | 5/2003 |
| WO | 03047467 | A1 | 6/2003 |
| WO | 03049619 | A2 | 6/2003 |
| WO | 03073910 | A2 | 9/2003 |
| WO | 03073913 | A2 | 9/2003 |
| WO | 03082129 | A2 | 10/2003 |
| WO | 03105667 | A2 | 12/2003 |
| WO | 2004004607 | A1 | 1/2004 |
| WO | 2004012583 | A2 | 2/2004 |
| WO | 2004012789 | A2 | 2/2004 |
| WO | 2004014282 | A2 | 2/2004 |
| WO | 2004019811 | A2 | 3/2004 |
| WO | 2004030570 | A2 | 4/2004 |
| WO | 2004037317 | A2 | 5/2004 |
| WO | 2004045370 | A2 | 6/2004 |
| WO | 2004045378 | A2 | 6/2004 |
| WO | 2004045463 | A2 | 6/2004 |
| WO | 2004047679 | A1 | 6/2004 |
| WO | 2004062725 | A1 | 7/2004 |
| WO | 2004082523 | A2 | 9/2004 |
| WO | 2004082538 | A2 | 9/2004 |
| WO | 2004093730 | A2 | 11/2004 |
| WO | 2004103162 | A2 | 12/2004 |
| WO | 2004112585 | A2 | 12/2004 |
| WO | 2004112651 | A2 | 12/2004 |
| WO | 2005002424 | A2 | 1/2005 |
| WO | 2005018507 | A2 | 3/2005 |
| WO | 2005027797 | A1 | 3/2005 |
| WO | 2005032421 | A2 | 4/2005 |
| WO | 2005062931 | A2 | 7/2005 |
| WO | 2005112792 | A2 | 12/2005 |
| WO | 2006037073 | A2 | 4/2006 |

(56) References Cited

FOREIGN PATENT DOCUMENTS

| | | | |
|---|---|---|---|
| WO | 2006105008 | A1 | 10/2006 |
| WO | 2006105009 | A1 | 10/2006 |
| WO | 2006115875 | A2 | 11/2006 |
| WO | 2006115876 | A2 | 11/2006 |
| WO | 2007009099 | A2 | 1/2007 |
| WO | 2007038608 | A2 | 4/2007 |
| WO | 2008140439 | A1 | 11/2008 |
| WO | 2010128502 | A1 | 11/2010 |
| WO | 2011034973 | A2 | 3/2011 |
| WO | 2011066533 | A1 | 6/2011 |
| WO | 2014138482 | A1 | 9/2014 |
| WO | 2016161135 | A1 | 10/2016 |
| WO | 2017015288 | A2 | 1/2017 |
| WO | 2018102310 | A1 | 6/2018 |
| WO | 2018106482 | A1 | 6/2018 |

OTHER PUBLICATIONS

Abe et al.“Updated: De Vega's annuloplasty for acquired tricuspid disease: Early and late results in 110 patients” Ann. Thorac. Surg. (1996) 62:1876-1877.

Agricola et al., “Mitral valve reserve in double orifice technique: an exercise echocardiographic study,” Journal of Heart Valve Disease(2002)11(5):637 643.

Alfieri et al., “An effective technique to correct anterior mitral leaflet prolapse,” J Card Surg(1999) 14(6):468-470.

Alfieri et al., “Novel suture device for beating heart mitral leaflet approximation,” Annals of Thoracic Surgery(2002) 74:1488 1493.

Alfieri et al., “The double orifice technique in mitral valve repair: a simple solution for complex problems,” Journal of Thoracic Cardiovascular Surgery(2001) 122:674 681.

Alfieri et al., “The edge to edge technique,” The European Association for Cardio-Thoracic Surgery 14th Annual Meeting, Oct. 7-11, 2000 Book of Proceedings. 3 pages.

Alfieri, “The edge-to-edge repair of the mitral valve,” [Abstract] 6th Annual NewEra Cardiac Care: Innovation & Tecnology, Heart Surgery Forum(2003) pp. 103.

Alvarez et al., “Repairing the degenerative mitral valve: Ten- to fifteen-year follow-up” J. Thorac. Cardiovasc. Surg. (1996) 112:238-247.

Arisi et al., “Mitral valve repair with Alfieri technique in mitral regurgitation of diverse etiology: early echocardiographic results,” Circulation Supplement II(2001) 104(17):3240.

Arthur C. Beall et al., Clinical Experience with a Dacron Velour-Covered Teflon-Disc Mitral Valve Prosthesis, 5 Ann. Thorac. Surg. 402-10 (1968).

Bach et al., “Early improvement in congestive heart failure after correction of secondary mitral regurgitation in end- stage cardiomyopathy,” Am. Heart J.(1995) 129:1165-1170.

Bach et al., “Improvement following correction of secondary mitral regurgitation in end-stage cardiomyopathy with mitral annuloplasty” Am. J. Cardiol. (1996) 78:966-969.

Bailey, “Surgery of the Heart,” Chapter 20(1995) pp. 686-737.

Bernal et al.“The ‘Valve Racket’: a new and different concept of atrioventricular valve repair,” Eur. J. Cardio-thoracic Surgery 29:1026-29 (2006).

Bhudia et al., “Edge-to-edge (Alfieri) mitral repair: results in diverse clinical settings,” Ann Thorac Surg, 77: 1598-1606 (2004).

Bhudia et al., “Edge-to-edge Mitral Repair: A Versatile Mitral Repair,” http://www.sts.org/doc/7007 accessed on Sep. 24, 2008.

Bhudia, #58 Edge-to-edge mitral repair: a versatile mitral repair technique, 2003 STS Presentation[Abstract Only]. 2 pages.

Bolling et al., Surgery for Acquired Heart Disease: Early Outcome of Mitral Valve Reconstruction in Patients with End-stage Cardiomyopathy, J. Thor. and Cariovasc. Surg., Apr. 1995, pp. 676-683, vol. 109.

Borghetti et al., “Preliminary observations on haemodynamics during physiological stress conditions following ‘double-orifice’ mitral valve repair,” European Journal of Cardio-thoracic Surgery, Apr. 18, 2001 20:262-269.

Castedo, “Edge-to-Edge Tricuspid Repair for Redeveloped Valve Incompetence after DeVega's Annuloplasty,” Ann Thora Surg., 75:605-606 (2003).

Copelan, “How Dr. Oz Kick-Started a Groundbreaking Device for Patients with Heart Failure,” Parade (Sep. 26, 2018).

Cribier et al., “Percutaneous Mechanical Mitral Commissurotomy With a Newly Designed Metallic Valvulotome: Immediate Results of the Initial Experience in 153 Patients,” Circulation 99:793-799 (1999).

Cribier, A., et al., “Percutaneous Mitral Valvotomy with a Metal Dilatator,” The Lancet 349:1667 (1997).

Dec et al., “Idiopathic dilated cardiomyopathy,” N. Engl. J. Med. (1994) 331:1564-1575. 12 pages.

Dias de Azeredo Bastos et al., “Percutaneous Mechanical Mitral Commissurotomy Performed With a Cribier's Metallic Valvulotome. Initial Results,” Arq Bras Cardiol, 77:126-131 (2001).

Dottori et al., “Echocardiographic imaging of the Alfieri type mitral valve repair,” Ital Heart J(2001) 2(4):319-320.

Downing et al., “Beating heart mitral valve surgery: Preliminary model and methodology,” Journal of Thoracic and Cardiovascular Surgery(2002) 123(6):1141-1146.

Falk et al., “Computer-Enhanced Mitral Valve Surgery: Toward a Total Endoscopic Procedure,” Seminars in Thoracic and Cardiovascular Surgery, 11(3):244-249 (1999).

Feldman, T., et al., “Technique of Percutaneous Transvenous Mitral Commissurotomy Using the Inoue Balloon Catheter,” Catheterization and Cardiovascular Diagnosis Supplement 2:26-34 (1994).

Filsoufi et al. “Restoring Optimal Surface of Coaptation With a Mini Leaflet Prosthesis: A New Surgical Concept for the Correction of Mitral Velve Prolapse,” Int'l. Soc. for Minimally Invasive Cardiothoracic Surgery 1(4):186-87 (2006).

Frazier et al., #62 Early Clinical Experience With an Implantable, Intracardiac Circulatory Support Device: Operative Considerations and Physiologic Implications, 2003 STS Presentation 1 page total. [Abstract Only].

Freeny et al., “Subselective Diagnostic and Interventional Arteriography Using a Simple Coaxial Catheter System,” Cardiovasc. Intervent. Radiol. 7:209-213 (1984).

Fucci et al., Improved Results with Mitral Valve Repair Using New Surgical Techniques, Eur. J. Cardiothorac. Surg., Nov. 1995, pp. 621-627, vol. 9.

Fundaro et al., “Chordal plication and free edge remodeling for mitral anterior leaflet prolapse repair: 8-year follow-up,” Annals of Thoracic Surgery(2001) 72:1515-1519.

Garcia-Rinaldi et al., “Left ventricular volume reduction and reconstruction is ischemic cardiomyopathy,” Journal of Cardiac Surgery(1999) 14:199-210.

Gateliene, “Early and postoperative results results of metal and tricuspid valve insufficiency surgical treatment using edge-to-edge central coaptation procedure,” Medicina 38 (Suppl 2): 172-175 (2002) [Article in LithuanianEnglish summary on p. 174 of the article].

Gatti et al.“The edge to edge technique as a trick to rescue an imperfect mitral valve repair,” Eur J Cardiothorac Surg. (2002) 22(5):817 20.

Gillinov et al., “Is Minimally Invasive Heart Valve Surgery a Paradigm for the Future?” Current Cardiology Reports, 1:318-322 (1999).

Glazier, J. and Turi, Z., “Percutaneous Balloon Mitral Valvuloplasty,” Progress in Cardiovascular Diseases 40(1):5-26 (1997).

Gregg W. Stone et al., Clinical Trial Design Principles and Endpoint Definitions for Transcatheter Mitral Valve Repair and Replacement: Part 1: Clinical Trial Design Principles: A Consensus Document from the Mitral Valve Academic Research Consortium, 66 J. Am. Coll. Cardiol. 278-307 (2015).

Gundry et al., “Facile Mitral Valve Repair Utilizing Leaflet Edge Approximation: Midterm Results of the Alfieri Figure of Eight Repair,” The Western Thoracic Surgical Association, Scientific Session (May 1999). 1 page.

Gupta et al., #61 Influence Of Older Donor Grafts on Heart Transplant Survival: Lack of Recipient Effects, 2003 STS Presentation[Abstract Only]. 1 page.

(56) References Cited

OTHER PUBLICATIONS

Hung et al., "Atrial Septal Puncture Technique in Percutaneous Transvenous Mitral Commissurotomy : Mitral Valvuloplasty Using the Inoue Balloon Catheter Technique," Catheterization and Cardiovascular Diagnosis 26: 275-284 (1992).
Hung et al., "Pitfalls and Tips in Inoue Balloon Mitral Commissurotomy," Catheterization and Cardiovascular Diagnosis, 37:188-199 (1996).
Ikeda et al., "Batista's operation with coronary artery bypass grafting and mitral valve plasty for ischemic dilated cardiomyopathy," The Japanese Journal of Thoracic and Cardiovascular Surgery(2000) 48:746-749.
Ing et al., "The Snare-Assisted Technique for Transcatheter Coil Occlusion of Moderate to Large Patent Ductus Arteriosus: Immediate and Intermediate Results," J. Am. Col. Cardiol. 33(6):1710-1718 (1999).
Inoue, K. and Feldman, T., "Percutaneous Transvenous Mitral Commissurotomy Using the Inoue Balloon Catheter," Catheterization and Cardiovascular Diagnosis 28:119-125 (1993).
Inoue, K., et al., "Clinical Application of Transvenous Mitral Commissurotomy by a New Balloon Catheter," J Thorac Cardiovasc Surg 87:394-402 (1984).
Izzat et al., "Early experience with partial left ventriculectomy in the Asia-Pacific Region," Annuals of Thoracic Surgery (1999) 67:1703-1707.
Källner et al., "Transaortic approach for the Alfieri Stitch," Ann Thorac Surg(2001) 71:378-380.
Kameda et al, Annuloplasty for Severe Mitral Regurgitation Due to Dilated Cardiomyopathy, Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al., "Blade atrial septostomy: Experience with the first 50 procedures" Cathet. Cardiovasc. Diagn(1991) 23:257-262.
Kherani et al., "Edge-to-edge mitral valve repair: the Columbia Presbyterian experience," Ann Thorac Surg2004; 78:73-76.
Konertz et at, "Results after partial left ventriculectomy in a European heart failure population," Journal of Cardiac Surgery(1999) 14(2):129-135.
Kron et al., "Surgical relocation of the posterior papillary muscle in chronic ischemic mitral regurgitation," Annals. of Thoracic Surgery(2002)74:600 601.
Krüger et al., "Edge to edge technique in complex mitral valve repair," Thorac Cardiovasc Surg, (2000) Thema: Posterhttp://www.thieme.de/thoracic/abstracts/abstracts/p-73.html.
Langer et al."Posterior mitral leaflet extensions: An adjunctive repair option for ischemic mitral regurgitation?," J. Thorac. Cardiovasc. Surf. 131:868-77 (2006).
Lau, K. and Hung, J., "Balloon Impasse'; A Marker for Severe Mitral Subvalvular Disease and a Predictor of Mitral Regurgitation in Inoue-Balloon Percutaneous Transvenous Mitral Commissurotomy," Catheterization and Cardiovascular Diagnosis 35:310-319 (1995).
Lock et al., "Transcatheter Closure of Atrial Septal Defects: Experimental Studies," Circulation 79:1091-1099 (1989).
Lorusso et al., "Double-Orifice" technique to repair extensive mitral valve excision following acute endocarditis, J Card Surg(1998) 13:24-26.
Lorusso et al., "The double-orifice technique for mitral valve construction: predictors of postoperative outcome," Eur J. Cardiothorac Surg(2001) 20(3):583-589.
Maisano et al., "The double orifice repair for Barlow Disease: a simple solution for a complex repair," Supplement I Circulation(1999) 100(18):I-94.
Maisano et al., "The double orifice technique as a standardized approach to treat mitral regurgitation due to severe myxomatous disease: surgical technique," European Journal of Cardiothoracic Surgery(2000) 17:201-215.
Maisano et al., "The edge-to-edge technique: A simplified method to correct mitral insufficiency" Eur. J. Cardiothorac. Surg.(1998) 13:240-246.
Maisano et al., "The hemodynamic effects of double-orifice valve repair for mitral regurgitation: a 3D computational model," European Journal of Cardio-thoracic Surgery(1999) 15:419-425.
Maisano et al., "Valve repair for traumatic tricuspid regurgitation," Eur J. Cardio-thorac Surg(1996) 10:867-873.
Mantovani et al., "Edge-to-edge repair of congenital familiar tricuspid regurgitation: case report," J. Heart Valve Dis. (2000) 9 (5):641-643.
McCarthy and Cosgrove et al."Tricuspid Valve Reapir with the Cosgrove-Edwards Annuloplasty System," Ann. Thorac. Surg. 64:267-268 (1997).
McCarthy et al., "Partial left ventriculectomy and mitral valve repair for end-stage congestive heart failure," European Journal of Cardio-thoracic Surgery(1998) 13:337-343.
McCarthy, P., et al., "Early Results with Partial Left Ventriculectomy," J Thorac Cardiovasc Surg 114(5):755-765 (1997).
Moainie et al., Correction of traumatic tricuspid regurgitation using the double orifice technique, Annals of Thoracic Surgery(2002) 73:963 965.
Morales et al., "Development of an off bypass mitral valve repair," The Heart Surgery Forum #1999-4963(1999) 2(2):115-120.
Netter, F. H., et al., "The Ciba Collection of Medical Illustrations," vol. 5. Royal Victorian Institute for the Blind Tertiary Resource Service, Melbourne (1969).
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al.., "Tricuspid Valve Incompetence Caused by Nonpenetrating Thoracic Trauma", Annals of Thoracic Surgery, 1991, 51 (2)320-322.
O'Rourke, R. and Crawford, M., "Mitral Valve Regurgitation," Year Book Medical Publishers, Inc. 1-52 (1984).
Osawa et al., "Partial Left Ventriculectomy in a 3-Year Old Boy with Dilated Cardiomyopathy," Japanese Journal of Thoracic and Cardiovascular Surg, 48:590-593 (2000).
Otto, Catherine M., "Timing of Surgery in Mitral Regurgitation," Heart 89:100-105 (2003).
Park et al."Clinical use of a blade atrial septostomy" Circulation (1978) 58:600-608.
Patel et al., #57 Epicardial Atrial Defibrillation: Novel Treatment of Postoperative Atrial Fibrillation, 2003 STS Presentation[Abstract Only]. 1 page.
Privitera et al."Mitral Valve Repair: Clinical Outcome and Pathology; Circulation," (2002) 106:173.
Rahhal, "Tiny device to 'zip up' leaky hearts invented by Dr Oz 20 years ago could save millions, study finds," Daily Mail (Sep. 26, 2018).
Randas J. V. Batista et al., Partial Left Ventriculectomy to Treat End-Stage Heart Disease, 64 Ann. Thorac. Surg. 634-38 (1997).
Redaelli et al., "A Computational Study of the Hemodynamics After 'Edge-To-Edge' Mitral Valve Repair," Journal of Biomechanical Engineering, 123:565-570 (2001).
Reul, "Mital valve reconstruction for mitral insufficiency," Progress in Cardiovascular Diseases, (1997) vol. XXXIX, No. 6pp. 567-599.
Ricchi et al., Linear Segmental Annuloplasty for Mitral Valve Repair, Ann. Thorac. Surg., Jan. 7, 1997, pp. 1805-1806, vol. 63.
Robicsek et al., #60 The Bicuspid Aortic Valve: How Does It Function? Why Does It Fail?, 2003 STS Presentation [Abstract Only]. 1 page.
Tager et al., Long-Term Follow-Up of Rheumatic Patients Undergoing Left-Sided Valve Replacement With Tricuspid Annuloplasty-Validity of Preoperative Echocardiographic Criteria in the Decision to Perform Tricuspid Annuloplasty, Am. J. Cardiol., Apr. 15, 1998, pp. 1013-1016, vol. 81.

(56) References Cited

OTHER PUBLICATIONS

Tamura et al., "Edge to Edge Repair for Mitral Regurgitation in a Patient with Chronic Hemodialysis: Report of A Case," Kyobu Geka. The Japanese Journal of Thoracic Surgery, 54(9):788-790 (2001).

Tibayan et al., #59 Annular Geometric Remodeling In Chronic Ischemic Mitral Regurgitation, 2003 STS Presentation [Abstract Only]. 2 pages.

Timek, "Edge-to-edge mitral repair: gradients and three-dimensional annular dynamics in vivo during inotropic stimulation," European Journal of Cardio-thoracic Surgery, (2001)19:431-437.

Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).

Totaro, "Mitral valve repair for isolated prolapse of the anterior leaflet: an 11-year follow-up," European Journal of Cardio-thoracic Surgery(1999) 15:119-126.

Uchida et al., "Percutaneous cardiomyotomy and valvultomy with angioscopic guidance," Am. Heart J.(1991) 121:1221-1224.

Umana et al., 'Bow-Tie' Mitral Valve Repair: An Adjuvant Technique for Ischemic Mitral Regurgitation, Ann. Thorac. Surg., May 12, 1998, pp. 1640-1646, vol. 66.

Umana et al., "'Bow-tie' Mitral Valve Repair Successfully Addresses Subvalvular Dysfunction in Ischemic Mitral Regurgitation," Surgical Forum, XLVIII:279-280 (1997).

Vismara et al., "Transcatheter Edge-to-Edge Treatment of Functional Tricuspid Regurgitation in an Ex Vivo Pulsatile Heart Model," JACC 68(10):1024-1033 (2016).

Votta et al., "3 D computational analysis of the stress distribution on the leaflets after edge to edge repair of mitral regurgitation," Journal of Heart Valve Disease(2002)11:810 822.

Waller et al., "Anatomic Basis for and Morphologic Results from Catheter Balloon Valvuloplasty of Stenotic Mitral Valves," Clin. Cardiol. 13:655-661 (1990).

Werker, P. and Kon M., "Review of Facilitated Approaches to Vascular Anastomosis Surgery," Ann Thorac Surg 63:122-7 (1997).

TISSUE FIXATION DEVICES AND METHODS

CROSS-REFERENCE TO RELATED APPLICATIONS

This application is a divisional of U.S. patent application Ser. No. 17/148,186, filed Jan. 13, 2021, which is a continuation of U.S. patent application Ser. No. 16/050,445, filed Jul. 31, 2018, now U.S. Pat. No. 10,893,941 which is a continuation of U.S. patent application Ser. No. 14/677,294, filed Apr. 2, 2015, now U.S. Pat. No. 10,524,912, the entire contents of which are incorporated by reference herein.

BACKGROUND

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves, and devices and methods for removing or disabling mitral valve repair components through minimally invasive procedures.

Surgical repair of bodily tissues often involves tissue approximation and fastening of such tissues in the approximated arrangement. When repairing valves, tissue approximation often includes coapting the leaflets of the valves in a therapeutic arrangement which may then be maintained by fastening or fixing the leaflets. Such fixation of the leaflets can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles themselves, or the left ventricular wall may be damaged or otherwise dysfunctional. Commonly, the valve annulus may be damaged, dilated, or weakened, limiting the ability of the mitral valve to close adequately against the high pressures of the left ventricle during systole.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bow-tie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

In some patients, a fixation device can be installed into the heart using minimally invasive techniques. The fixation device can hold the adjacent segments of the opposed valve leaflets together to reduce mitral valve regurgitation. One such device used to clip the anterior and posterior leaflets of the mitral valve together is the MitraClip® fixation device, sold by Abbott Vascular, Santa Clara, California, USA.

These fixation devices often include clips designed to grip and hold against tissue as the clip arms are moved and positioned against the tissue at the treatment site and then closed against the tissue. Such clips are designed to continue gripping the tissue as the fixation device is closed into a final position. In order to achieve this effect, such these clips are sometimes equipped with barbs or hooks to grip the tissue as the clip is flexed into position against the tissue.

However, some tissue fixation treatments require a fixation device to move through a wide range of grasping angles in order to be properly positioned relative to the target tissue and then to grasp the tissue and bring it to a closed position. This moving and plastically deforming components of the fixation device during positioning and closure of the device can lead to the weakening and pre-mature degradation of the fixation device. Additionally, some tissue fixation treatments require that the fixation device maintain a degree of flexibility and mobility to allow a range of physiological movement even after the device has been properly placed and the target tissue has been properly fixed into the desired position, This can increase the risk of pre-mature failure of the device as continued plastic deformation of the flexing components (e.g., from the continuous opening and closing of valve leaflets) leads to unfavorable degradation of the device.

For these reasons, there is an ongoing need to provide alternative and additional methods, devices, and systems for tissue fixation that provide beneficial elasticity and durability of the flexing components without unduly increasing the associated manufacturing costs of the flexing components. There is also a need to provide such methods, devices, and systems in a manner that does not limit the tissue gripping ability of the tissue fixation device. At least some of the embodiments disclosed below are directed toward these objectives.

DESCRIPTION OF THE BACKGROUND ART

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759; WO 2000/060995; WO 2004/103162. Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorac. Surg. 66:1640-1646, describe open surgical procedures for performing "edge-to-edge" or "bow-tie" mitral valve repair where edges of the opposed valve leaflets are sutured together to lessen regurgitation. Dec and Fuster (1994) N. Engl. J. Med. 331:1564-1575 and Alvarez et al. (1996) J. Thorac. Cardiovasc. Surg. 112:238-247 are review articles discussing the nature of and treatments for dilated cardiomyopathy.

Mitral valve annuloplasty is described in the following publications: Bach and Bolling (1996) Am. J. Cardiol. 78:966-969; Kameda et al. (1996) Ann. Thorac. Surg. 61:1829-1832; Bach and Bolling (1995) Am. Heart J. 129:1165-1170; and Bolling et al. (1995) 109:676-683. Linear segmental annuloplasty for mitral valve repair is described in Ricchi et al. (1997) Ann. Thorac. Surg. 63:1805-1806. Tricuspid valve annuloplasty is described in McCarthy and Cosgrove (1997) Ann. Thorac. Surg. 64:267-268; Tager et al. (1998) Am. J. Cardiol. 81:1013-1016; and Abe et al. (1989) Ann. Thorac. Surg. 48:670-676.

Percutaneous transluminal cardiac repair procedures are described in Park et al. (1978) Circulation 58:600-608; Uchida et al. (1991) Am. Heart J. 121: 1221-1224; and Ali Khan et al. (1991) Cathet. Cardiovasc. Diagn. 23:257-262. Endovascular cardiac valve replacement is described in U.S. Pat. Nos. 5,840,081; 5,411,552; 5,554,185; 5,332,402; 4,994,077; and 4,056,854. U.S. Pat. No. 3,671,979 describes a catheter for temporary placement of an artificial heart valve.

Other percutaneous and endovascular cardiac repair procedures are described in U.S. Pat. Nos. 4,917,089; 4,484, 579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769, 812; and 5,718,725.

BRIEF SUMMARY

The present disclosure describes methods and devices for gripping tissue in a tissue repair and/or fixation procedure, such as in a mitral valve repair procedure. Certain embodiments of a tissue gripping device include a flexible member formed from a shape-memory material, the flexible member comprising a base section and an arm, the arm having a first end connected to the base section, a free end extending away from the base section, and an attachment surface disposed between the joining end and the free end, and at least one tissue gripping member formed from a second material, the second material being more rigid than the shape-memory material, the tissue gripping member comprising a mating surface coupled to the attachment surface of the arm to join the tissue gripping member to the flexible member, and a tissue gripping surface disposed opposite the mating surface, the tissue gripping surface including a frictional element configured to resist movement of tissue away from the tissue gripping surface after the tissue has contacted the tissue gripping surface.

Certain embodiments of a tissue fixation system configured for intravascular delivery and for use in joining mitral valve tissue for treatment of the mitral valve include: a body; a proximal element comprising a flexible member formed from a shape-memory material, the flexible member comprising a base section and an arm, the arm having a first end connected to the base section, a free end extending away from the base section, and an attachment surface disposed between the joining end and the free end, and at least one tissue gripping member formed from a second material, the second material being more rigid than the shape-memory material, the tissue gripping member comprising a mating surface coupled to the attachment surface of the arm to join the tissue gripping member to the flexible member, and a tissue gripping surface disposed opposite the mating surface, the tissue gripping surface including a frictional element configured to resist movement of tissue away from the tissue gripping surface after the tissue has contacted the tissue gripping surface; and a distal element having a first end pivotally coupled to the body and extending to a free second end and a tissue engagement surface between the first and second end, the tissue engagement surface being configured to approximate and engage a portion of the leaflets of the mitral valve, wherein the proximal element is configured to cooperate with the distal element to form a space for receiving a portion of mitral valve tissue therebetween.

Certain embodiments of a method of manufacturing a tissue gripping device of the present disclosure include: forming a flexible member from a shape-memory alloy by cutting a pattern shape and heat shape setting at least one bend feature, the flexible member comprising a base section and an arm, the arm having a first end connected to the base section, a free end extending away from the base section, and an attachment surface disposed between the joining end and the free end, the at least one bend feature being disposed between the first end and the free end of the arm; forming a tissue gripping member from a second material by die stamping the second material to form a plurality of raised barbs and a plurality of slotted recesses along the side edge of the tissue gripping member, the second material being more rigid than the shape-memory material, the tissue gripping member comprising a mating surface and a tissue gripping surface disposed opposite the mating surface; and attaching the tissue gripping member to the flexible member by coupling the mating surface of the tissue gripping member to the attachment surface of the arm.

Certain embodiments provide advantages and benefits over tissue gripping devices, systems, and methods of the prior art. For example, providing a flexible member formed from a shape-memory material may provide superelasticity over the wide range of grasping angles covered during positioning of a tissue gripping device at a treatment site, such as during mitral valve leaflet grasp attempts during a mitral valve repair procedure. Additionally, avoiding plastic deformation of the flexible member during positioning and/or during post-implanting movement can increase the function and/or life of the device. Furthermore, embodiments providing one or more tissue gripping members formed from a second material can provide easier and more cost-effective manufacturing of tissue gripping frictional elements and other features of the tissue gripping member(s) as opposed to forming them using a shape-memory material, such as by forming them directly on the flexible member. Certain embodiment may therefore provide the benefits of superelastic properties where such properties are desired, while simultaneously providing more rigidity and/or easier manufacturability where such properties are desired.

These and other objects and features of the present disclosure will become more fully apparent from the following description and appended claims, or may be learned by the practice of the embodiments of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which.

DETAILED DESCRIPTION

I. Cardiac Physiology

Figure 1:
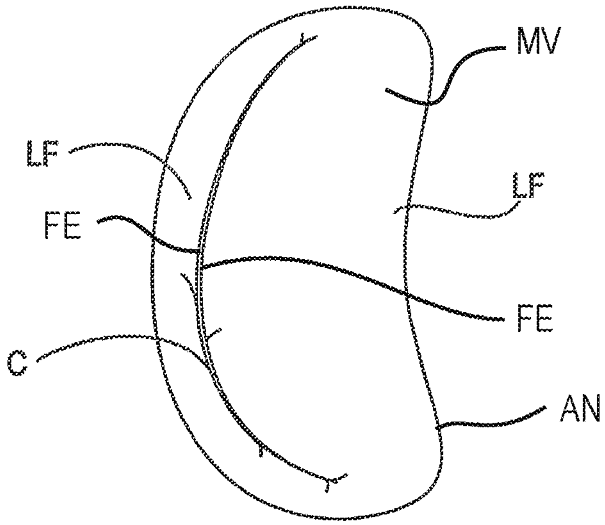
FIG. 1 illustrates free edges of leaflets of the mitral valve in normal coaptation.
Figure 2:
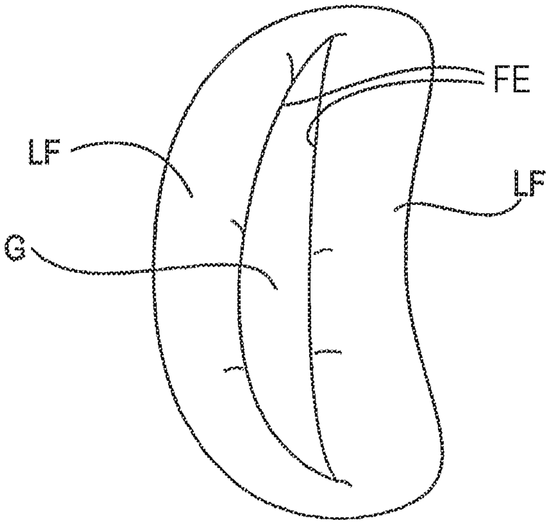
FIG. 2 illustrates the free edges in regurgitative coaptation.

As shown in FIG. 1, the mitral valve (MV) comprises a pair of leaflets (LF) having free edges (FE) which, in patients with normal heart structure and function, meet evenly to close along a line of coaption (C). The leaflets (LF) attach to the surrounding heart structure along an annular region called the annulus (AN). The free edges (FE) of the leaflets (LF) are secured to the lower portions of the left ventricle LV through chordae tendinae (or "chordae"). As the left ventricle of a heart contracts (which is called "systole"), blood flow from the left ventricle to the left atrium through the mitral valve (MV) (called "mitral regurgitation") is usually prevented by the mitral valve. Regurgitation occurs when the valve leaflets do not close properly and allow leakage from the left ventricle into the left atrium. A number of heart structural defects can cause mitral regurgitation. FIG. 2 shows a mitral valve with a defect causing regurgitation through a gap (G).

II. Overview of Mitral Valve Fixation System

Several methods for repairing or replacing a defective mitral valve exist. Some defects in the mitral valve can be treated through intravascular procedures, where interventional tools and devices are introduced and removed from the heart through the blood vessels. One method of repairing certain mitral valve defects includes intravascular delivery of a fixation device to hold portions of the mitral valve tissues in a certain position. One or more interventional catheters may be used to deliver a fixation device to the mitral valve and install it there as an implant to treat mitral regurgitation.

Figure 3A:
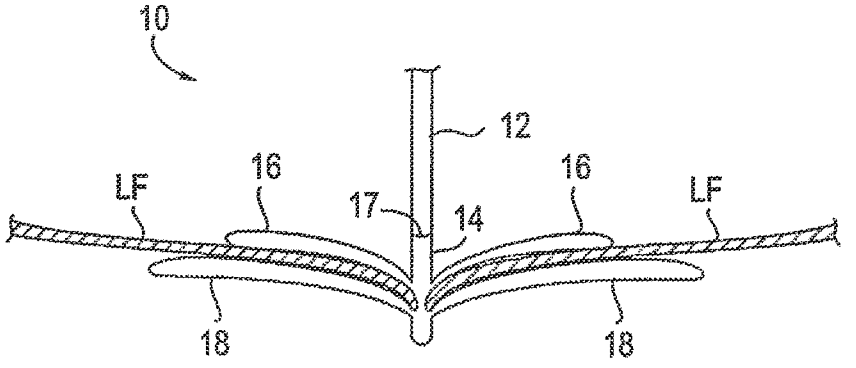
FIGS. 3A-3C illustrate grasping of the leaflets with a fixation assembly, inversion of the distal elements of the fixation assembly and removal of the fixation assembly, respectively.

FIG. 3A illustrates a schematic of an interventional tool 10 with a delivery shaft 12 and a fixation device 14. The tool 10 has approached the mitral valve MV from the atrial side and grasped the leaflets LF. The fixation device 14 is releasably attached to the shaft 12 of the interventional tool 10 at the distal end of the shaft 12. In this application, when describing devices, "proximal" means the direction toward the end of the device to be manipulated by the user outside the patient's body, and "distal" means the direction toward the working end of the device that is positioned at the treatment site and away from the user. When describing the mitral valve, proximal means the atrial side of the leaflets and distal means the ventricular side of the leaflets. The fixation device 14 comprises proximal elements 16 and distal elements 18 which protrude radially outward and are positionable on opposite sides of the leaflets LF as shown so as to capture or retain the leaflets therebetween. The fixation device 14 is coupleable to the shaft 12 by a coupling mechanism 17.

Figure 3B:
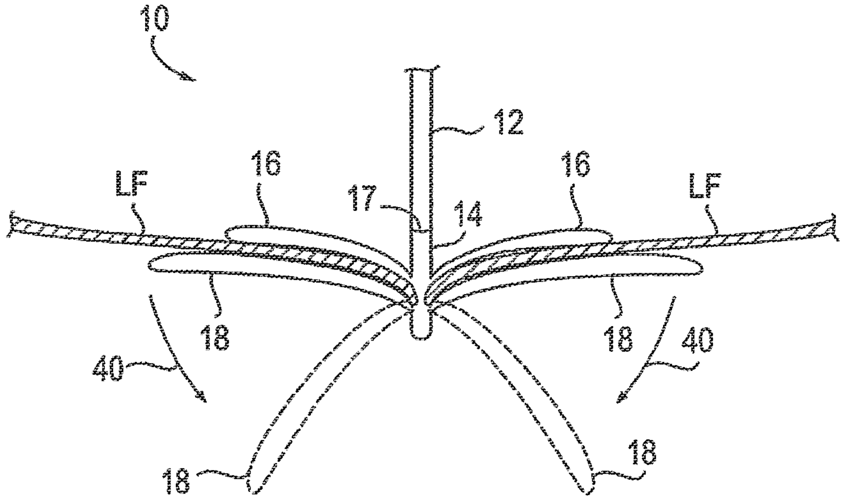
Figure 3C:
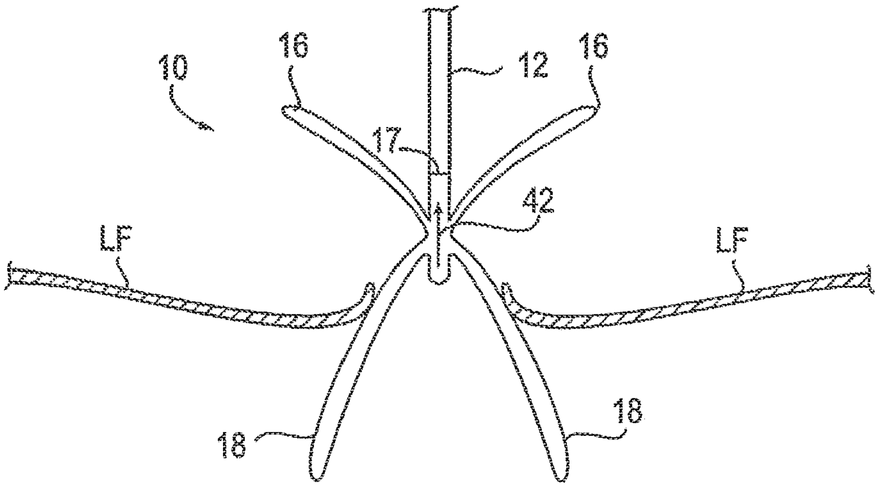

FIG. 3B illustrates that the distal elements 18 may be moved in the direction of arrows 40 to an inverted position. The proximal elements 16 may be raised as shown in FIG. 3C. In the inverted position, the device 14 may be repositioned and then be reverted to a grasping position against the leaflets as in FIG. 3A. Or, the fixation device 14 may be withdrawn (indicated by arrow 42) from the leaflets as shown in FIG. 3C. Such inversion reduces trauma to the leaflets and minimizes any entanglement of the device with surrounding tissues.

Figure 4:
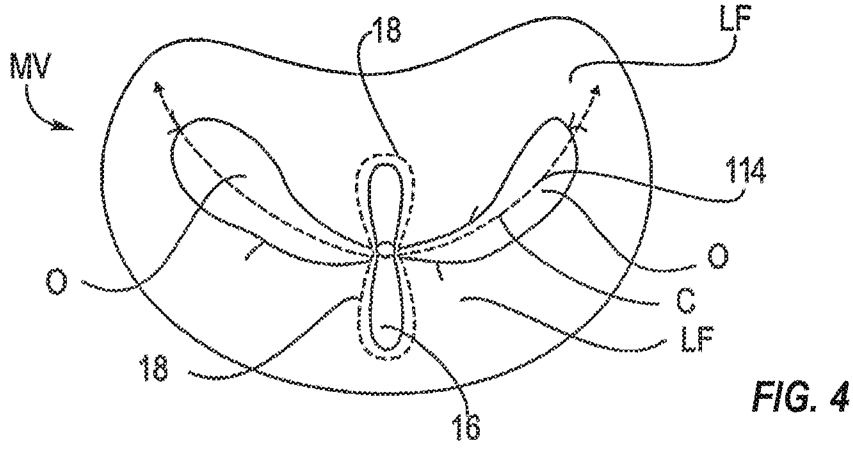
FIG. 4 illustrates the fixation assembly in a desired orientation relative to the leaflets.

FIG. 4 illustrates the fixation device 14 in a desired orientation in relation to the leaflets LF. The mitral valve MV is viewed from the atrial side, so the proximal elements 16 are shown in solid line and the distal elements 18 are shown in dashed line. The proximal and distal elements 16, 18 are positioned to be substantially perpendicular to the line of coaptation C. During diastole (when blood is flowing from the left atrium to the left ventricle), fixation device 14 holds the leaflets LF in position between the elements 16, 18 surrounded by openings or orifices O which result from the diastolic pressure gradient, as shown in FIG. 4. Once the leaflets are coapted in the desired arrangement, the fixation device 14 is detached from the shaft 12 and left behind as an implant.

Figure 5:
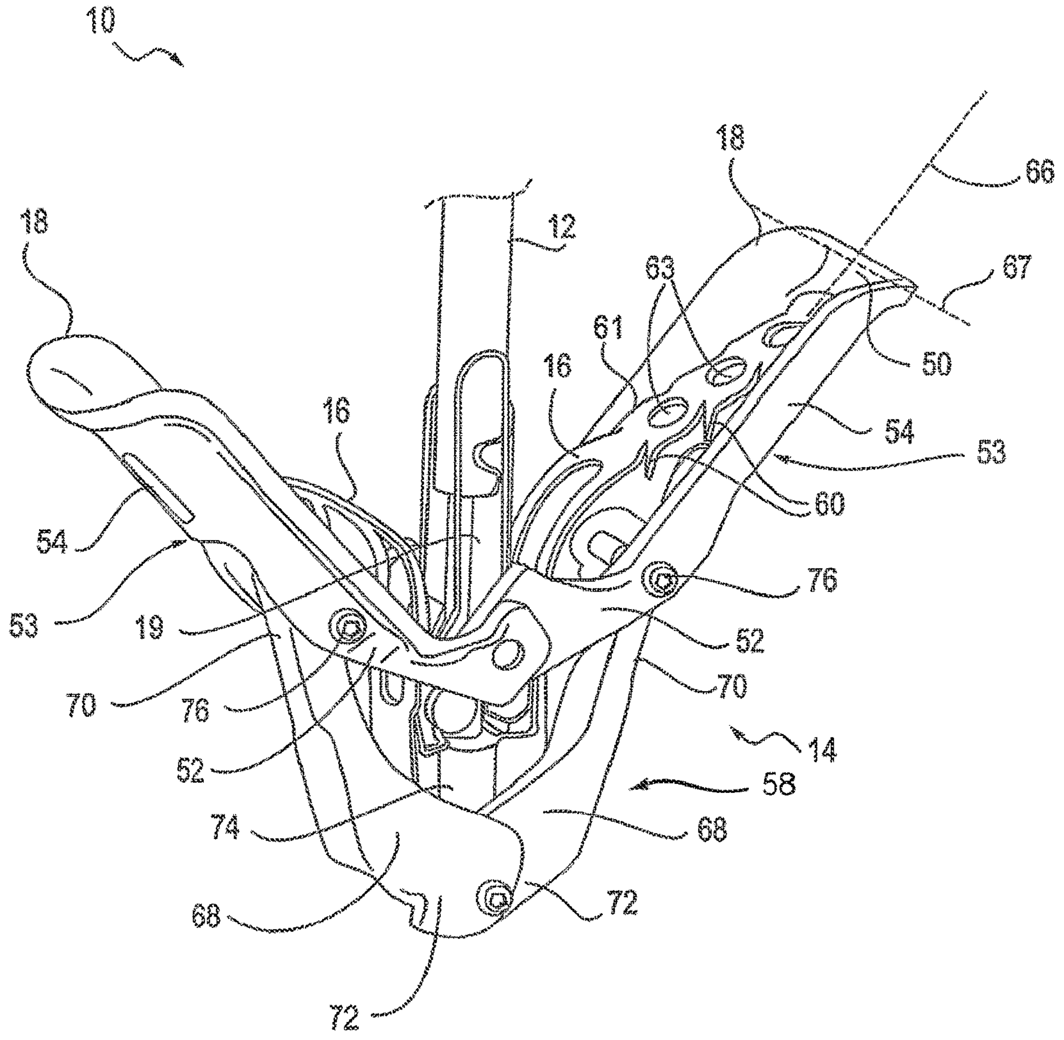
FIG. 5 illustrates an exemplary fixation assembly coupled to a shaft.

FIG. 5 illustrates an exemplary fixation device 14. The fixation device 14 is shown coupled to a shaft 12 to form an interventional tool 10. The fixation device 14 includes a coupling member 19, a pair of opposed proximal elements 16, and a pair of opposed distal elements 18. The distal elements 18 comprise elongate arms 53, each arm having a proximal end 52 rotatably connected to the coupling member 19 and a free end 54. Preferably, each free end 54 defines a curvature about two axes, axis 66 perpendicular to longitudinal axis of arms 53, and axis 67 perpendicular to axis 66 or the longitudinal axis of arms 53. Arms 53 have engagement surfaces 50. Arms 53 and engagement surfaces 50 are configured to engage about 4-10 mm of tissue, and preferably about 6-8 mm along the longitudinal axis of arms 53. Arms 53 further include a plurality of openings.

The proximal elements 16 are preferably resiliently biased toward the distal elements 18. When the fixation device 14 is in the open position, each proximal element 16 is separated from the engagement surface 50 near the proximal end 52 of arm 53 and slopes toward the engagement surface 50 near the free end 54 with the free end of the proximal element 16 contacting engagement surface 50, as illustrated in FIG. 5. Proximal elements 16 include a plurality of openings 63 and scalloped side edges 61 to increase their grip on tissue. The proximal elements 16 optionally include a frictional element or multiple frictional elements to assist in grasping the leaflets. The frictional elements may comprise barbs 60 having tapering pointed tips extending toward engagement surfaces 50. Any suitable frictional elements may be used, such as prongs, windings, bands, barbs, grooves, channels, bumps, surface roughening, sintering, high-friction pads, coverings, coatings or a combination of these. The proximal elements 16 may be covered with a fabric or other flexible material. Preferably, when fabrics or coverings are used in combination with barbs or other frictional features, such features will protrude through such fabric or other covering so as to contact any tissue engaged by proximal elements 16.

The fixation device 14 also includes an actuator or actuation mechanism 58. The actuation mechanism 58 comprises two link members or legs 68, each leg 68 having a first end 70 which is rotatably joined with one of the distal elements 18 at a riveted joint 76 and a second end 72 which is rotatably joined with a stud 74. The actuation mechanism 58 comprises two legs 68 which are each movably coupled to a base 69. Or, each leg 68 may be individually attached to the stud 74 by a separate rivet or pin. The stud 74 is joinable with an actuator rod which extends through the shaft 12 and is axially extendable and retractable to move the stud 74 and therefore the legs 68 which rotate the distal elements 18 between closed, open and inverted positions. Immobilization of the stud 74 holds the legs 68 in place and therefore holds the distal elements 18 in a desired position. The stud 74 may also be locked in place by a locking feature. This actuator rod and stud assembly may be considered a first means for selectively moving the distal elements between a first position in which the distal elements are in a collapsed, low profile configuration for delivery of the device, a second position in which the distal elements are in an expanded configuration for positioning the device relative to the mitral valve, and a third position in which the distal elements are secured in position against a portion of the leaflets adjacent the mitral valve on the ventricular side.

Figure 6A:
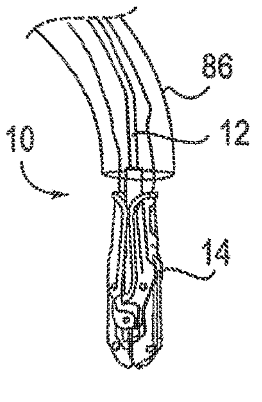
FIGS. 6A-6B, 7A-7C, and 8 illustrate a fixation assembly in various possible positions during introduction and placement of the assembly within the body to perform a therapeutic procedure.

FIGS. 6A-6B, 7A-7C, and 8 illustrate various possible positions of the fixation device 14 of FIG. 5. FIG. 6A illustrates an interventional tool 10 delivered through a catheter 86. The catheter 86 may take the form of a guide catheter or sheath. The interventional tool 10 comprises a fixation device 14 coupled to a shaft 12 and the fixation device 14 is shown in the closed position.

Figure 6B:
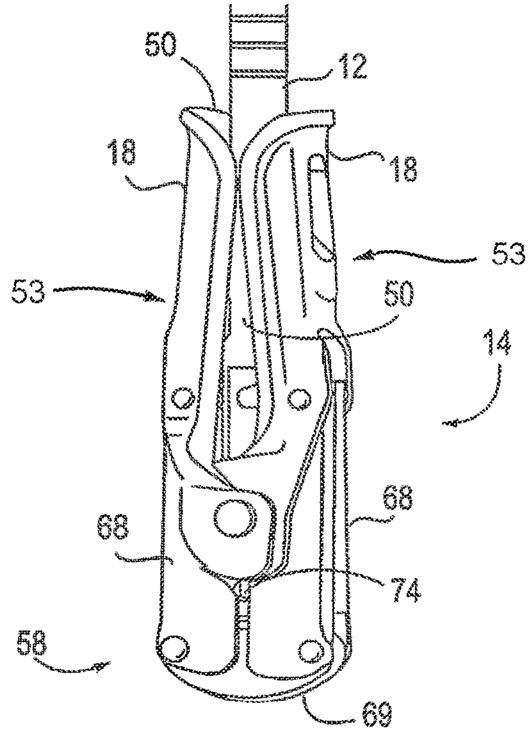

FIG. 6B illustrates a device similar to the device of FIG. 6A in a larger view. In the closed position, the opposed pair of distal elements 18 are positioned so that the engagement surfaces 50 face each other. Each distal element 18 comprises an elongate arm 53 having a cupped or concave shape so that together the arms 53 surround the shaft 12. This provides a low profile for the fixation device 14.

Figure 7A:
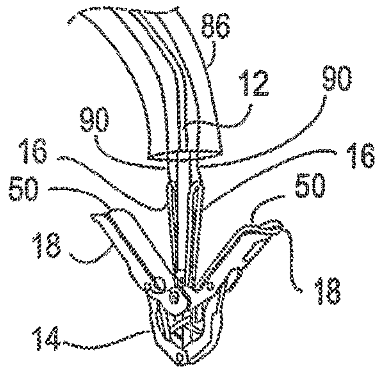
Figure 7B:
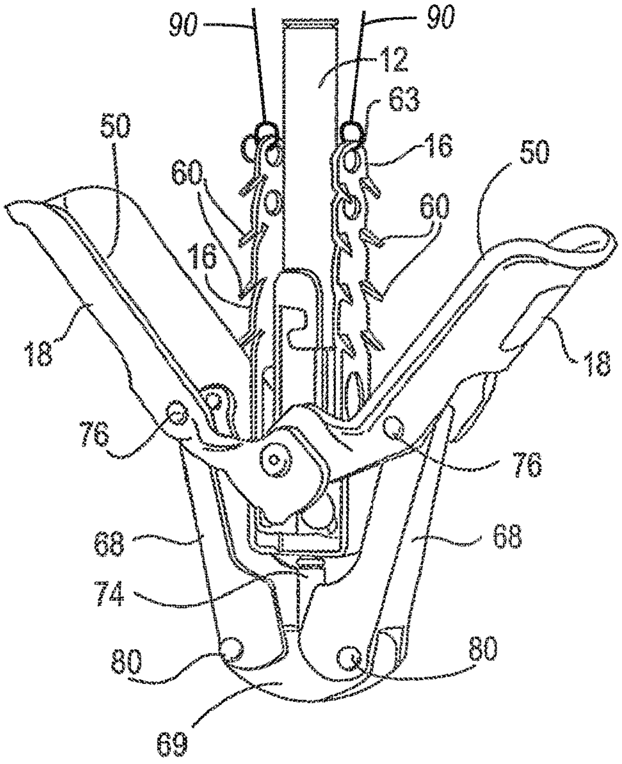

FIGS. 7A-7B illustrate the fixation device 14 in the open position. In the open position, the distal elements 18 are rotated so that the engagement surfaces 50 face a first direction. Distal advancement of the actuator rod relative to shaft 12, and thus distal advancement of the stud 74 relative to coupling member 19, applies force to the distal elements 18 which begin to rotate around joints 76. Such rotation and movement of the distal elements 18 radially outward causes rotation of the legs 68 about joints 80 so that the legs 68 are directed slightly outwards. The stud 74 may be advanced to any desired distance correlating to a desired separation of the distal elements 18. In the open position, engagement surfaces 50 are disposed at an acute angle relative to shaft 12, and are preferably at an angle of between 90 and 180 degrees relative to each other. In the open position, the free ends 54 of arms 53 may have a span therebetween of about 10-20 mm, usually about 12-18 mm, and preferably about 14-16 mm.

Figure 7C:
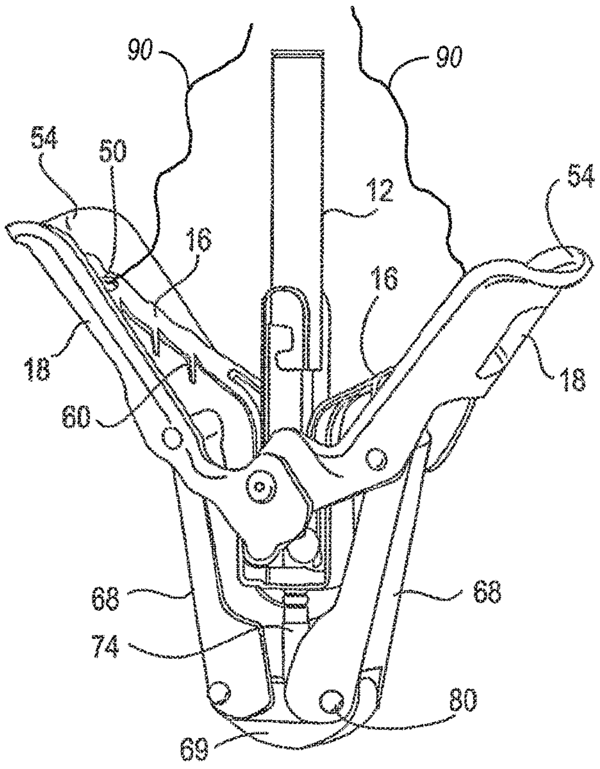

Proximal elements 16 are typically biased outwardly toward arms 53. The proximal elements 16 may be moved inwardly toward the shaft 12 and held against the shaft 12 with the aid of proximal element lines 90 which can be in the form of sutures, wires, nitinol wire, rods, cables, polymeric lines, or other suitable structures. The proximal element lines 90 extend through the shaft 302 of the delivery catheter 300 and connect with the proximal elements 16. The proximal elements 16 are raised and lowered by manipulation of the proximal element lines 90. For example, FIG. 7C illustrates proximal elements 16 in a lowered position as a result of providing slack to proximal element lines 90. Once the device is properly positioned and deployed, the proximal element lines can be removed by withdrawing them through the catheter and out the proximal end of the device 10. The proximal element lines 90 may be considered a second means for selectively moving the proximal elements between a first position in which the proximal elements are in a collapsed, low profile configuration for delivery of the device and a second position in which the proximal elements are in an expanded configuration for engaging a portion of the leaflets adjacent the mitral valve on the atrial side.

In the open position, the fixation device 14 can engage the tissue which is to be approximated or treated. The interventional tool 10 is advanced through the mitral valve from the left atrium to the left ventricle. The distal elements 18 are then deployed by advancing actuator rod relative to shaft 12 to thereby reorient distal elements 18 to be perpendicular to the line of coaptation. The entire assembly is then withdrawn proximally and positioned so that the engagement surfaces 50 contact the ventricular surface of the valve leaflets, thereby engaging the left ventricle side surfaces of the leaflets. The proximal elements 16 remain on the atrial side of the valve leaflets so that the leaflets lie between the proximal and distal elements. The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 8:
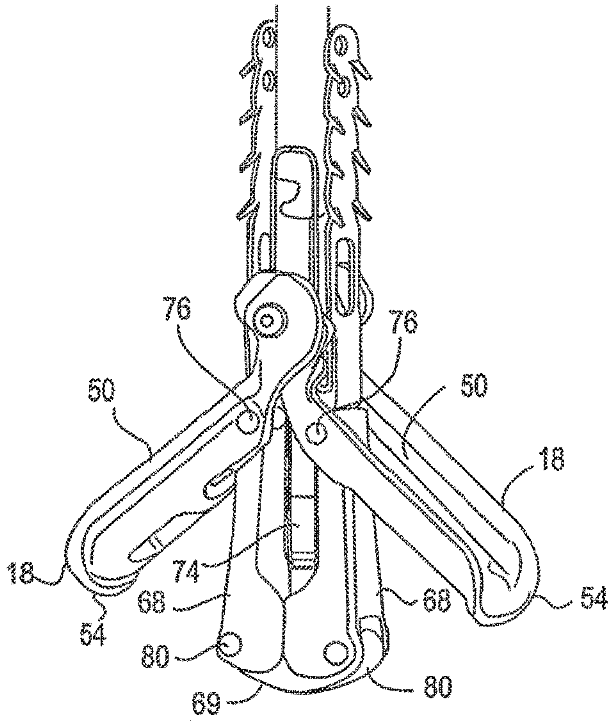

It may also be desired to invert distal elements 18 of the fixation device 14 to aid in repositioning or removal of the fixation device 14. FIG. 8 illustrates the fixation device 14 in the inverted position. By further advancement of actuator rod relative to shaft 12, and thus stud 74 relative to coupling member 19, the distal elements 18 are further rotated so that the engagement surfaces 50 face outwardly and free ends 54 point distally, with each arm 53 forming an obtuse angle relative to shaft 12.

The angle between arms 53 when the device is inverted is preferably in the range of about 270 to 360 degrees. Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm. Barbs 60 are angled slightly in the distal direction (away from the free ends of the proximal elements 16), reducing the risk that the barbs will catch on or lacerate tissue as the fixation device is withdrawn.

Once the distal elements 18 of the fixation device 14 have been positioned in a desired location against the left ventricle side surfaces of the valve leaflets, the leaflets may then be captured between the proximal elements 16 and the distal elements 18. The proximal elements 16 are lowered toward the engagement surfaces 50 by releasing tension from proximal element lines 90, thereby releasing proximal elements 16 so that they are then free to move, in response to the internal spring bias force formed into proximal elements 16, from a constrained, collapsed position to an expanded, deployed position and so that the leaflets are held between the proximal elements 16 and the distal elements 18. If regurgitation is not sufficiently reduced, the proximal elements 16 may be raised and the distal elements 18 adjusted or inverted to reposition the fixation device 14.

After the leaflets have been captured between the proximal and distal elements 16, 18 in a desired arrangement, the distal elements 18 may be locked to hold the leaflets LF in this position or the fixation device 14 may be returned to or toward a closed position. This is achieved by retraction of the stud 74 proximally relative to coupling member 19 so that the legs 68 of the actuation mechanism 58 apply an upwards force to the distal elements 18 which in turn rotate the distal elements 18 so that the engagement surfaces 50 again face one another. The released proximal elements 16 which are biased outwardly toward distal elements 18 are concurrently urged inwardly by the distal elements 18. The fixation device 14 may then be locked to hold the leaflets in this closed position. The fixation device 14 may then be released from the shaft 12.

The fixation device 14 optionally includes a locking mechanism for locking the device 14 in a particular position, such as an open, closed or inverted position or any position therebetween. The locking mechanism may include a release harness. Applying tension to the release harness may unlock the locking mechanism. The lock lines 92 engage the release harnesses 108 of the locking mechanism 106 to lock and unlock the locking mechanism 106. The lock lines 92 extend through the shaft 302 of the delivery catheter 300. A handle attached to the proximal end of the shaft is used to manipulate and decouple the fixation device 14.

Additional disclosure regarding such fixation devices 14 may be found in PCT Publication No. WO 2004/103162 and U.S. patent application Ser. No. 14/216,787, the disclosures of both of which are incorporated herein in their entirety.

III. Improved Tissue Fixation Device

Certain embodiments of tissue fixation devices of the present disclosure include a proximal element 16 formed as a tissue gripping device as described in detail below. In some embodiments, a tissue gripping device can form the proximal element 16 of a tissue fixation device (such as any of the tissue fixation devices 14 described above with reference to FIGS. 3-8 and related discussion), and can be utilized as the proximal element 16 of the tissue fixation device. The terms "tissue gripping device" and "proximal element" or "proximal elements," as defined herein, are therefore interchangeable.

Figure 9A:
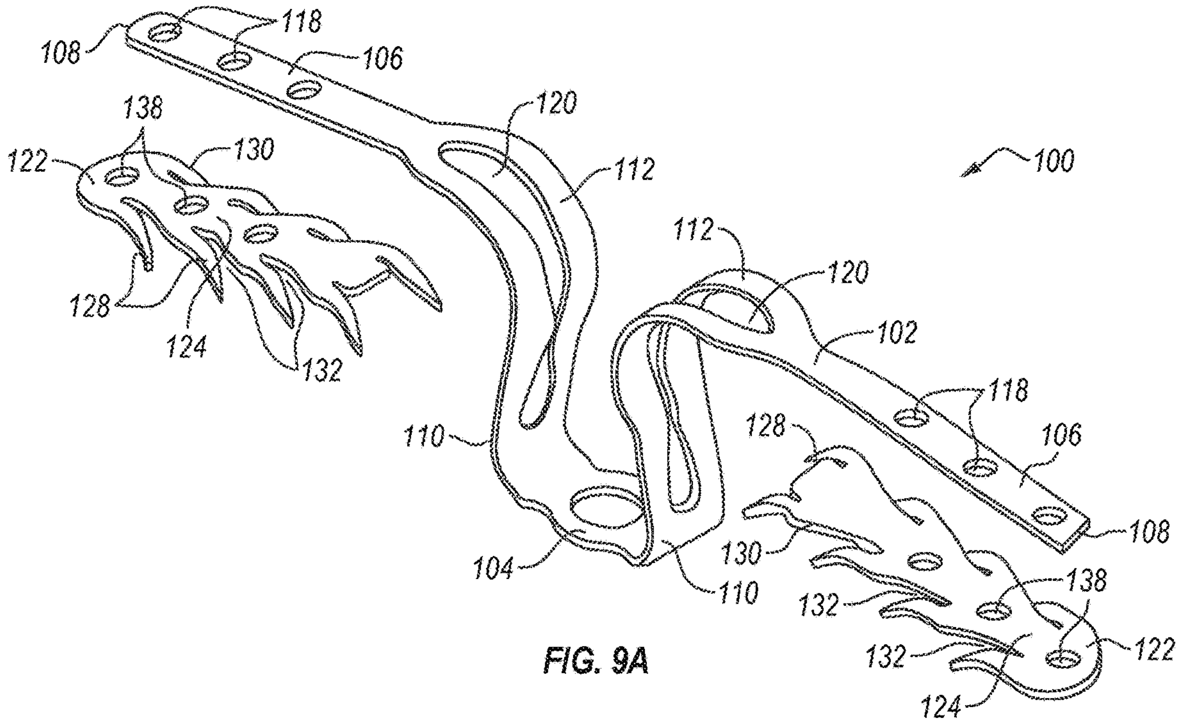
FIGS. 9A-9C illustrate detailed views of a proximal element of a tissue fixation device, the proximal element including a flexible member and a plurality of tissue gripping members.
Figure 9B:
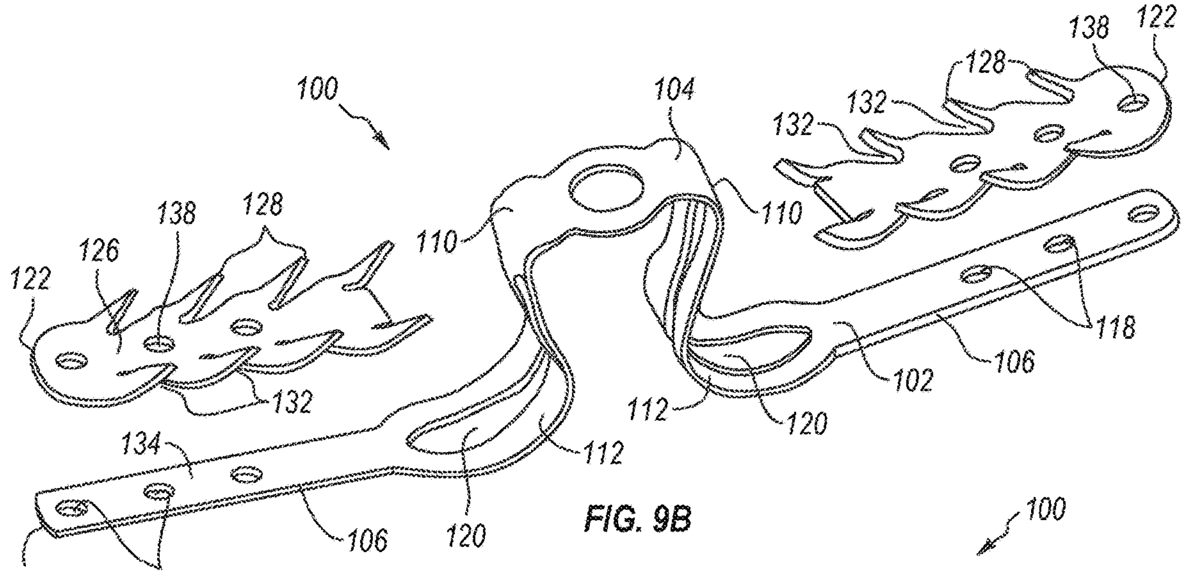
Figure 9C:
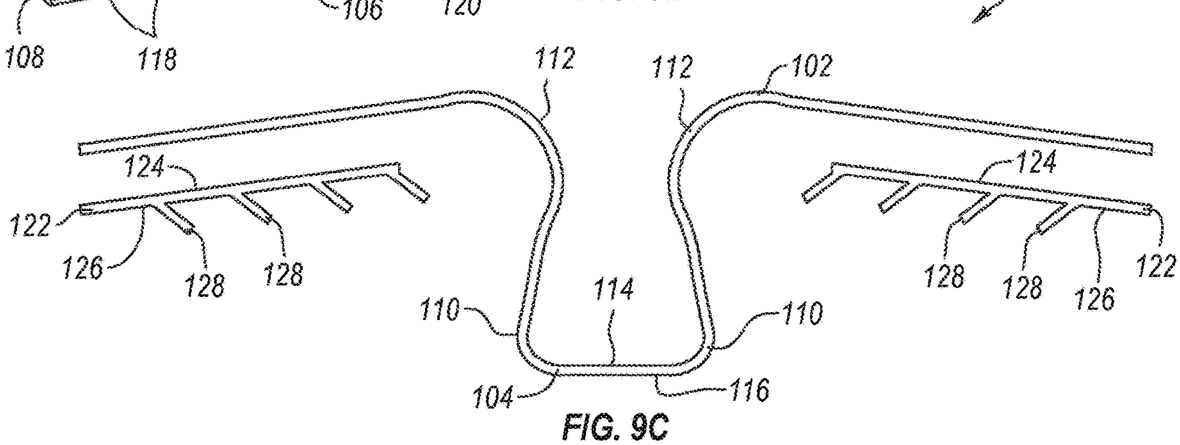

FIGS. 9A-9C illustrate an embodiment of a tissue gripping device 100 including a flexible member 102 and at least one tissue gripping member 122 (e.g., a pair of tissue gripping members 122 as illustrated) coupled to the flexible member 102. The flexible member 102 may be formed from a first material and the tissue gripping member 122 may be formed from a second, different material. In preferred embodiments, the second material has greater rigidity than the first material, making the tissue gripping member 122 more rigid than the flexible member 102. Accordingly, in such embodiments, the flexible member 102 is more flexible than the tissue gripping member 122. The flexible member 102 is preferably made from a shape-memory material such as nitinol. In this configuration, flexible member 102 exhibits its superelasticity during flexing, bending, and/or otherwise positioning the tissue gripping device 100 (e.g., such as during positioning and deployment of the device at a treatment site and/or during continued movement after being deployed).

For example, during a mitral valve repair procedure, portions of the tissue gripping device may need to repeatedly pass through wide angles as multiple tissue grasping attempts are made and/or as the tissue gripping device 100 is moved into an acceptable position against the leaflets of the mitral valve. Furthermore, even after deployment against mitral valve tissue, the tissue gripping device 100 may need to provide some amount of flexibility and movement as the repaired mitral valve tissue continues to move during cardiac cycles. Forming the flexible member 102 from a shape-memory material such as nitinol avoids plastic deformation of the flexible member 102 during these movements, thereby promoting easier tissue grasping during deployment and reducing mechanical degradation of the tissue gripping device 100 from repeated and/or high levels of plastic deformation.

The tissue gripping member 122 can be formed from stainless steel or a cobalt-chromium alloy, such as a cobalt-chromium-nickel alloy or a cobalt-chromium-nickel-iron-molybdenum-manganese alloy. In preferred embodiments, the tissue gripping member 122 is formed from Elgiloy®, however, any suitable material or combinations of materials may be used. For example, a tissue gripping member 122 may be formed from a material in which frictional elements 128 (e.g., raised barbs) or other features of the tissue gripping member(s) are easily machined or otherwise formed (e.g., more easily machined relative to machining such features using a shape-memory material such as with machining frictional elements 128 directly onto the arms 106 of the flexible member 102).

The flexible member 102 includes a proximal side 114, a distal side 116, a base section 104, and a pair of arms 106, with each arm 106 extending from the base section 104 to a free end 108. In other embodiments, there may be one arm extending from a base section, or there may be more than two arms extending from a base section. For example, some embodiments may have multiple arms arrayed about a base section (e.g., in a radial fashion), and/or may include a first plurality of arms disposed opposite a second plurality of arms.

Each arm in the illustrated embodiment includes a first bend feature 110 disposed at an area adjacent to the base section 104, and a second bend feature 112 disposed a distance farther toward the free end 106 from the first bend feature 110. The first bend features 110 form angles of about 90 degrees or just under 90 degrees (e.g., about 60 to 120 degrees, about 70 to 110 degrees, or about 80 to 100 degrees) as measured from the proximal side 114, and the second bend features 112 form angles of about 90 degrees or just under 90 degrees (e.g., about 60 to 120 degrees, about 70 to 110 degrees, or about 80 to 100 degrees) as measured from the distal side 116.

The first and second bend features 110 and 112 are configured to give the flexible member 102 a bent configuration when the flexible member 102 is in a relaxed state, such that when the flexible member 102 is forced into a stressed state (e.g., by bending the flexible member 102 at one or more of the first and/or second bend features 110 and 112), the flexible member 102 is resiliently biased toward the relaxed state.

For example, an arm 106 may be deformed at the second bend feature 112 in a manner that flexes the arm 106 in a proximal direction and an inward direction, thereby flexing the arm 106 toward a straighter configuration (e.g., increasing the angle of the second bend feature 112 as measured from the distal side 116). In such a position, the flexible member 102 is in a stressed state such that the arm 106 of the flexible member 102 is resiliently biased toward a distal direction and an outward direction. Other embodiments may omit one or more of the bend features, and other embodiments may include additional bend features. These and other embodiments may include bend features with differing bend angles when in a relaxed state. For example, some embodiments may include bend features that measure greater than about 90 degrees or less than about 90 degrees when in a relaxed state.

The flexible member 102 of the illustrated embodiment includes a plurality of holes 118 distributed along the length of each arm 106. The holes 118 are configured to provide a passage or tie point for one or more sutures, wires, nitinol wires, rods, cables, polymeric lines, or other such structures. As discussed above, these materials may be coupled to one or more arms 106 to operate as proximal element lines (e.g., element lines 90 illustrated in FIGS. 7A-7C) for raising, lowering, and otherwise manipulating, positioning and/or deploying the flexible member 102. Additionally, or alternatively, the holes 118 may be configured to provide for the coupling of the flexible member 102 to one or more tissue gripping members (as discussed in detail below).

Other embodiments may include a flexible member with more or less holes and/or with holes in other positions of the flexible member. For example, some embodiments may omit holes completely, and some embodiments may include only one hole and/or only one hole per arm. Other embodiments may include holes of different shapes and/or sizes, such as holes formed as slots, slits, or other shapes. In embodiments where more than one hole is included, the holes may be uniform in size, shape, and distribution or may be non-uniform in one or more of size, shape, and distribution.

Each arm 106 of the illustrated embodiment includes a furcated section 120. The furcated section 120 may extend from the base section 104 to a position farther along the arm 106 toward the free end 108 of the arm 106, as illustrated. In other embodiments, a furcated section may be positioned at other locations along an arm and/or base section. Other embodiments may include one or more furcated sections extending completely to the free end of an arm, thereby forming a bifurcated or fork-shaped arm. Other embodiments omit any furcated sections. The furcated sections 120 of the illustrated embodiment coincide with the second bend features 112. The furcated sections 120 may be configured (e.g., in size, shape, spacing, position, etc.) so as to provide desired resiliency and/or flexibility at the coinciding second bend features 112.

The illustrated embodiment includes a pair of tissue gripping members 122, each having a mating surface 124 and a tissue gripping surface 126. Each tissue gripping member 122 includes a plurality of frictional elements 128 configured to engage with tissue at a treatment site and resist movement of tissue away from the tissue gripping member after the frictional elements 128 have engaged with the tissue. As shown in the illustrated embodiment, the frictional elements 128 are formed as angled barbs extending distally and inwardly. In this manner, tissue that is engaged with the frictional elements 128 of a tissue gripping member 122 is prevented from moving proximally and outwardly relative to the tissue gripping member 122.

The frictional elements 128 of the illustrated tissue gripping members 122 protrude from a side edge 130 of the tissue gripping members 122, thereby forming a plurality of slotted recesses 132 disposed along each side edges 130 of each tissue gripping member 122 at sections adjacent to the frictional elements 128. Other embodiments may include only one tissue gripping member or may include more than two tissue gripping members. For example, some embodiments may include multiple, separately formed tissue gripping members configured to be coupled to each arm. In other embodiments, not every arm includes a corresponding tissue gripping member. Other embodiments may include frictional elements of varying size, number, and/or shape. For example, in some embodiments the frictional elements may be formed as posts, tines, prongs, bands, grooves, channels, bumps, pads, or a combination of these or any other feature suitable for increasing friction and/or gripping of contacted tissue.

The tissue gripping members 122 of the illustrated embodiment include a plurality of holes 138 distributed along the length of each tissue gripping member 122. As with the holes 118 of the flexible member 102, the holes 138 of the tissue gripping members 122 are configured to provide a passage or tie point for one or more sutures, wires, nitinol wires, rods, cables, polymeric lines, or other such structures to operate as proximal element lines (e.g., element lines 90 illustrated in FIGS. 7A-7C) and/or to provide for the coupling of one or more of the tissue gripping members 122 to the flexible member 102.

The holes 138 of the tissue gripping member 122 of the illustrated embodiment are formed so as to coincide with the holes 118 of the flexible member 102. In this manner, the tissue gripping member 122 may be positioned relative to the flexible member 102 such that each of the holes 138 of the tissue gripping member 122 align with a corresponding hole 118 of the flexible member 102.

Other embodiments may include a tissue gripping member with more or less holes and/or with holes in other positions of the tissue gripping member. For example, some tissue gripping members may omit holes, or may include only one hole. Other embodiments may include holes of different shapes and/or sizes, such as slots, slits, or other shapes. In embodiments where more than one hole is included, the holes may be uniform in size, shape, and distribution or may be non-uniform in one or more of size, shape, and distribution. In other embodiments, not every hole of the tissue gripping member is configured to align with a corresponding hole of the flexible member and vice versa. In some embodiments, no holes are aligned when the tissue gripping member is properly positioned relative to the flexible member.

In the illustrated embodiment, the distal side of each arm 106 of the flexible member 102 includes an attachment surface 134. The tissue gripping member 122 is positioned on the distal side of the arm 106 of the flexible member 102, with the mating surface 124 of the tissue gripping member 122 facing the attachment surface 134. The tissue gripping member 122 is joined to the flexible member 102 by coupling the mating surface 124 to the attachment surface 134. In other embodiments, the mating surface and the attachment surface may be formed with corresponding press-fit portions or other locking/engaging portions configured to allow the tissue gripping member to be joined to the flexible member by engaging the corresponding press-fit portions and/or other corresponding locking portions. In some embodiments, the tissue gripping member may be fastened to the flexible member by using an adhesive or by welding, soldering, bolting, clamping, riveting, crimping or otherwise securing the tissue gripping member to the flexible member.

In some embodiments, an arm of the flexible member is configured to bend proximally while moving from a relaxed configuration toward a stressed configuration, and to resiliently flex distally toward a relaxed configuration when positioned in a stressed configuration, thereby forcing the attachment surface of the arm against the tissue gripping member as the arm flexed distally toward a relaxed configuration. For example, when a tissue gripping device is properly positioned and deployed at a mitral valve, the arm of the flexible member will operate to "sandwich" the tissue gripping member between the arm and the mitral valve tissue being gripped.

Figure 10A:
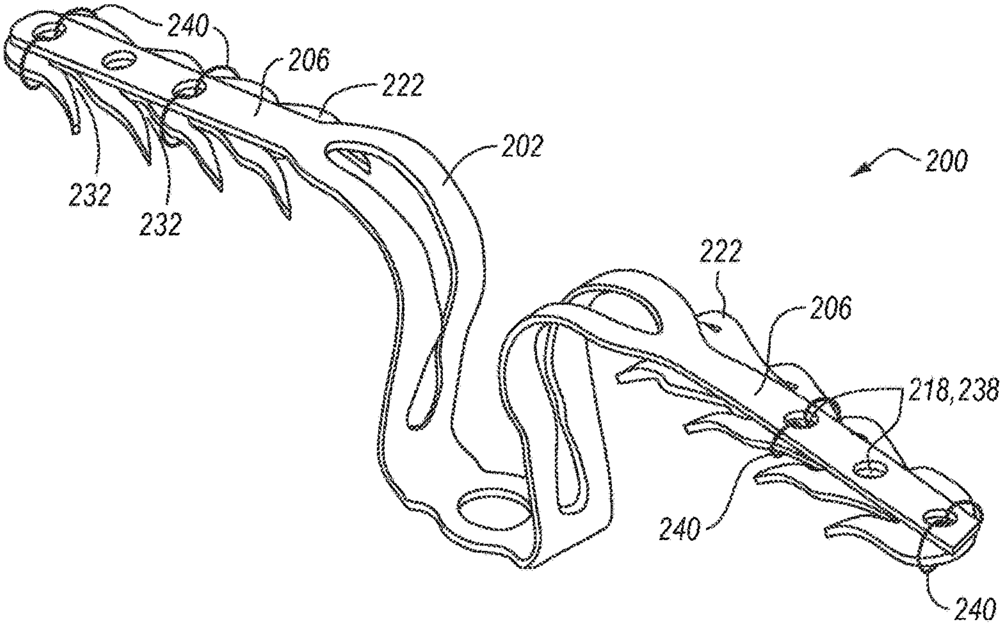
FIGS. 10A-10C illustrate detailed views of a proximal element of a tissue fixation device, with a plurality of tissue gripping members joined to a flexible member by suture lines.
Figure 10B:
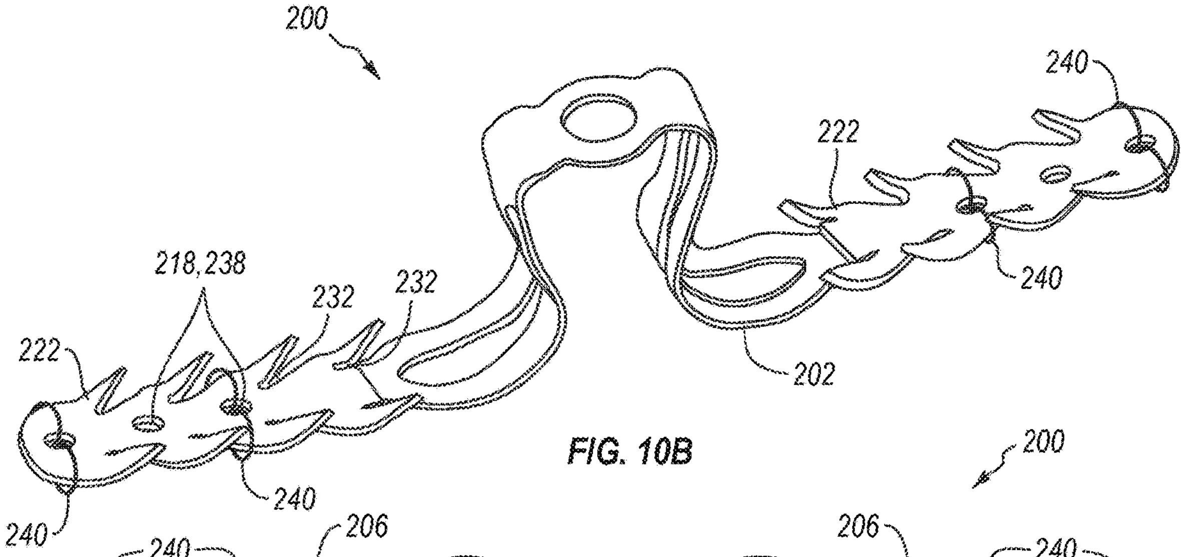
Figure 10C:
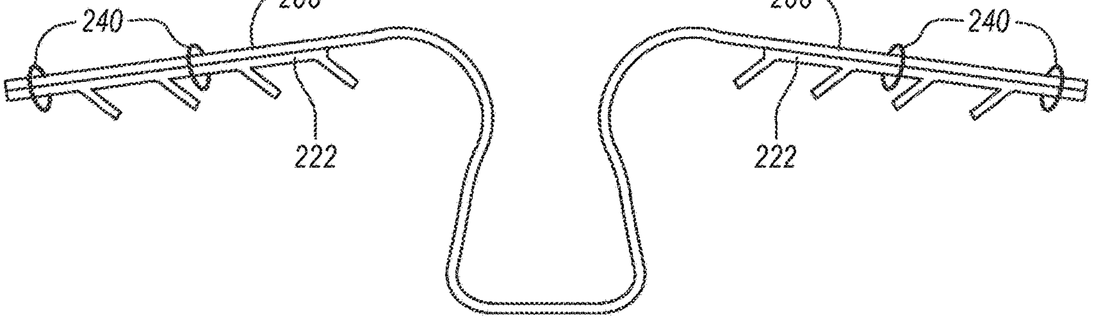

FIGS. 10A-10C illustrate an embodiment of a tissue gripping device 200 wherein the tissue gripping members 222 have been coupled to the flexible member 202. In the illustrated embodiment, each tissue gripping member 222 has been positioned next to the flexible member 202 by joining each mating surface (not shown) of each tissue gripping member 222 to one of the corresponding attachment surfaces (not shown) of the flexible member 202. In the illustrated embodiment, the tissue gripping members 222 are secured to the flexible member 202 by forming suture loops 240 through the aligned holes 218 and 238 of the flexible member 202 and the tissue gripping members 222, respectively. In this configuration, the suture loops 240 can fasten the tissue gripping member 222 to the flexible member 202 by encircling at least a portion of the tissue gripping member and at least a portion of the arm 206 of the flexible member 202 before being tied off, tightened, or otherwise secured so as to hold the tissue gripping member 222 in position against the flexible member 202.

In other embodiments, one or more suture lines may be used to tie or fasten one or more tissue gripping members to the flexible member in other configurations. For example, one or more suture lines may be threaded or laced through multiple holes on both the tissue gripping member and the flexible member before being tied off, tightened, or otherwise set in place in order to secure the tissue gripping member to the flexible member. In other embodiments, one or more suture lines do not pass through any holes. In such embodiments, suture lines may be looped or wrapped around the arm of the flexible member and the tissue gripping member to secure the tissue gripping member to the arm.

The suture line forming the suture loops 240 or other suture fastening structures may be wrapped and/or threaded a single time or multiple times before being tied, tightened, or otherwise set in place. For example, some suture lines may be wrapped repeatedly and/or may double back on themselves in order to strengthen or further secure the coupling of a tissue gripping member to an arm. In some embodiments one or more of the suture lines used to form the suture loops 240 or other suture fastening structures may also extend from the tissue gripping device 200 to act as the element lines described above (e.g., element lines 90 illustrated in FIGS. 7A-7C).

The tissue gripping members 222 of the illustrated embodiment also include a plurality of slotted recesses 232. In embodiments such as this, one or more suture loops 240 may be formed such that the suture line passes through and lodges within oppositely disposed slotted recesses 232, thereby further aiding in the securing of the tissue gripping member 222 to the arm 206 as well as promoting proper placement of the suture loop 240 and preventing slippage, loosening, or unraveling of the inner suture loop 240 from its proper position.

In other embodiments, suture loops or other suture fastening structures do not pass through or lodge within any slotted recesses. Some embodiments may include suture loops and/or suture fastening structures that pass through and/or lodge within one or more (not necessarily oppositely disposed) slotted recesses to aid in fastening the tissue gripping member to the arm of the flexible member. Yet other embodiments may include suture lines forming suture loops or other suture fastening structures that pass through and/or lodge within one or more slotted recesses but do not pass through any holes. Conversely, some embodiments may include suture lines forming suture loops or other suture fastening structures that pass through one or more holes but do not pass thorough and/or lodge within any slotted recess.

The illustrated embodiment includes two suture loops 240 at each tissue gripping member 222. In other embodiments, more or fewer suture loops or suture fastening structures may be used, though in preferred embodiments, at least two fastening points are formed (e.g., by using two or more suture loops or by threading or lacing a suture line across multiple points) in order to prevent rotational slippage of the tissue gripping member from the flexible member due to moment forces.

Figure 11A:
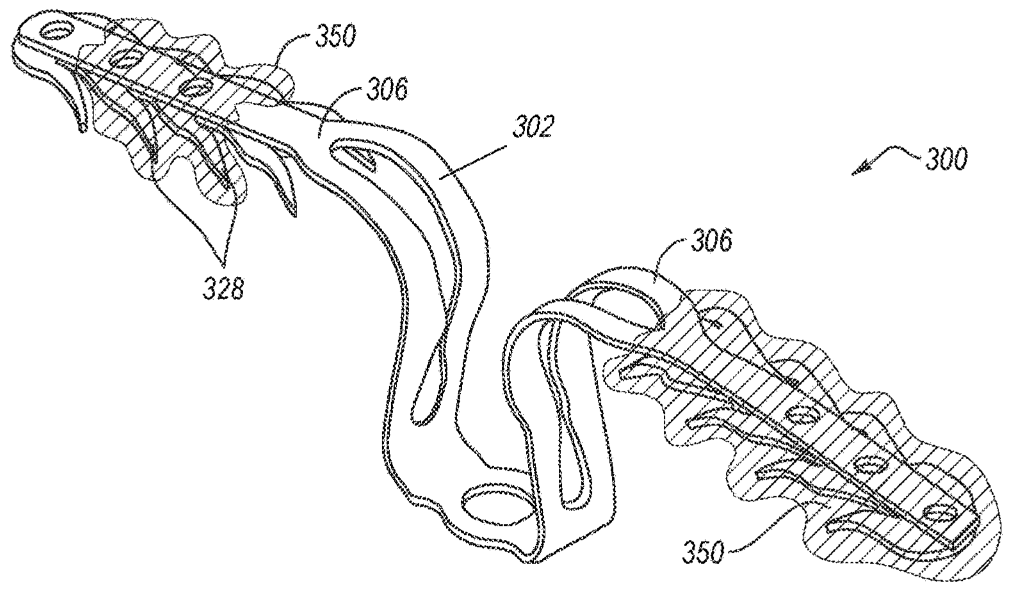
FIGS. 11A-11C illustrate detailed views of a proximal element of a tissue fixation device, the proximal element having a cover, and a plurality of tissue gripping members held against a flexible member by the cover.
Figure 11B:
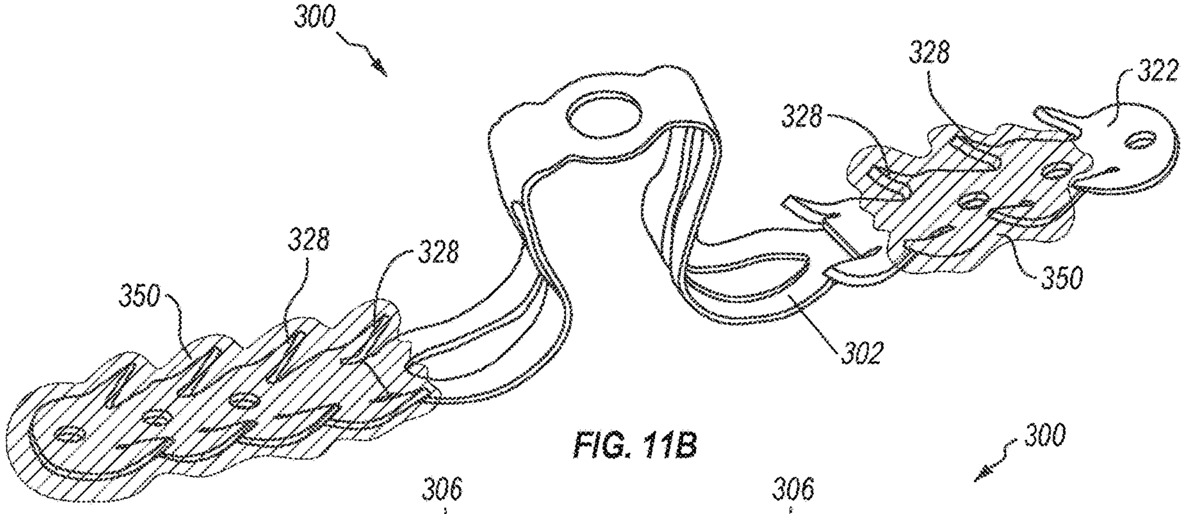
Figure 11C:
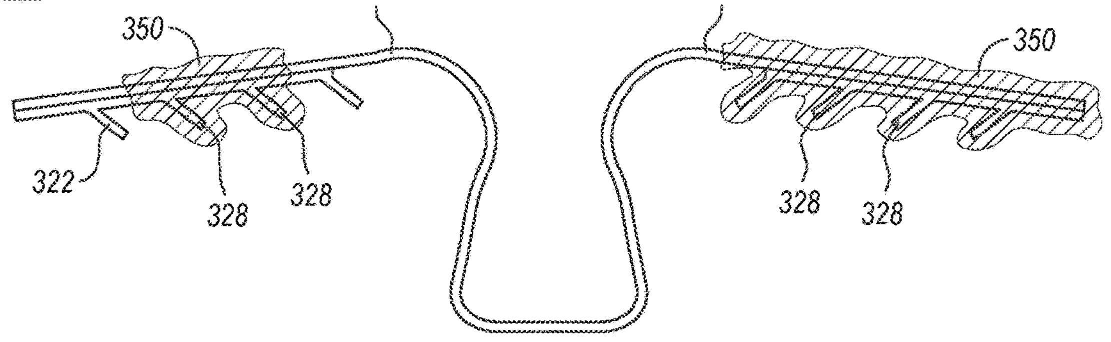

FIGS. 11A-11C illustrate an embodiment of a tissue gripping device 300 wherein the tissue gripping members 322 have been coupled to the flexible member 302 using at least one cover 350. The cover 350 is positioned over at least a portion of the arm 306 of the flexible member 302 and over at least a portion of the tissue gripping member 322 so as to hold the tissue gripping member 322 against the arm 306.

In preferred embodiments, the cover 350 is formed as a polymer cover which may be formed on the tissue gripping device 300 by dipping, spraying, coating or otherwise adhering it to the surfaces of the tissue gripping device 300 or to portions of the tissue gripping device 300. In some embodiments, the polymer coating may be applied to the tissue gripping member 322 and the arm 306 (or portions thereof) while the tissue gripping member 322 is held in place against the flexible member 306. The polymer coating may then cure, harden, and/or solidify to form the cover 350 and to hold the tissue gripping member 322 against the flexible member 302. In other embodiments, a polymer coating may act as an adhesive, and the polymer coating may be applied to the mating surface (not shown) and/or attachment surface (not shown) in order to adhere the tissue gripping member 322 to the arm 306 as the mating surface is positioned against the attachment surface and the polymer coating is cured.

The cover 350 may be formed in whole or in part of polyethylene terephtalate, polyester, cotton, polyurethane, expanded polytetrafluoroethylene (ePTFE), silicon, or various biocompatible polymers or fibers and have any suitable form, such as a fabric, mesh, textured weave, felt, looped or porous structure. The cover 350 may also be configured to leave the frictional elements 328 (in embodiments that include them) exposed. The cover 350 may also include drugs, antibiotics, anti-thrombosis agents, or anti-platelet agents such as heparin or warfarin sodium. These agents may be impregnated in and/or coated on the cover 350 such that they are delivered to surrounding tissues and/or the blood stream when the tissue gripping device 300 is implanted into a patient.

The embodiment illustrated in FIGS. 11A-11C include some covers 350 that are positioned over the entirety of each tissue gripping member 322 and the portion of the arms 306 adjacent to each tissue gripping member 322. In other embodiments that include a cover, the cover may be positioned to cover more of the tissue gripping device or even the entirety of the tissue gripping device (e.g., the entire device may be sprayed, dipped, or otherwise coated in a polymer coating that forms the cover). Alternatively, some embodiments may include a cover (such as some of the covers 350 illustrated in FIGS. 11A-11C) positioned over less of the tissue gripping device such that other portions of the tissue gripping member and/or arm are exposed (e.g., inner and/or outer portions).

In some embodiments, one or more tissue gripping members may be coupled to an arm of the flexible member using suture lines as discussed with respect to FIGS. 10A-10C in addition to being held in place using a cover as discussed with respect to FIGS. 11A-11C. For example, one or more suture loops and/or suture fastening structures may be used to fasten one or more tissue gripping members to the flexible member. Afterwards (or alternatively before or at the same time), a polymer coating may be applied to form a cover surrounding at least a portion of the tissue gripping member and at least a portion of the coinciding arm.

IV. Methods of Manufacture

Embodiments of tissue gripping devices of the present disclosure may be manufactured by forming a flexible member from a shape-memory material (such as nitinol). Forming the flexible member may be accomplished by cutting a pattern shape from of shape-memory material sheet stock (or alternatively strip or band stock or other forms of stock). Various features (e.g., furcated sections, holes, etc.) may optionally be formed in the flexible member either during or after the initial formation of the flexible element from the stock material. This may be accomplished using any suitable subtractive manufacturing process such as drilling, lathing, die stamping, cutting, or the like. In some embodiments, other features may be added using an additive manufacturing process. In other embodiments, no additional features or elements are formed through any subtractive or additive manufacturing process.

In some embodiments, the flexible member may be further processed through a shape setting process. For example, one or more bend features may be formed in the flexible member by subjecting the flexible member to a heated shape setting process in order to set the shape of the bend in the shape-memory material of the flexible member.

In some embodiments, one or more tissue gripping members are formed separate from the flexible member. Forming the tissue gripping member(s) may be accomplished through a cutting and/or progressive die stamping process of a material having a suitable machinability profile for such a manufacturing process. For example, the material from which the one or more tissue gripping members are formed may be obtained by cutting and/or die stamping a shape from sheet stock (or alternatively strip or band stock or other forms of stock). For example, stock material may be stainless steel or a cobalt-chromium alloy, such as a cobalt-chromium-nickel alloy or a cobalt-chromium-nickel-iron-molybdenum-manganese alloy. In preferred embodiments, the tissue gripping member is formed from Elgiloy®. Various features (e.g., holes, frictional elements, slotted recesses, etc.) may be formed on the tissue gripping member as it is formed from the stock material.

In some embodiments, the tissue gripping member may be further manufactured through a single or progressive die stamping process. For example, the tissue gripping member may be subjected to a progressive die stamping process in order to form and/or further define a variety of features on the tissue gripping member, such as a plurality of raised barbs and slotted recesses.

In some embodiments, after formation of the flexible member and the tissue gripping member, the tissue gripping member is attached to the flexible member by coupling a mating surface of the tissue gripping member (e.g., mating surface 124 of the embodiment of FIGS. 9A-9C) to an attachment surface (e.g., attachment surface 134 of the embodiment of FIGS. 9A-9C) of the flexible member. The tissue gripping member may then be further secured to the flexible member.

For example, one or more suture lines may be wrapped or threaded around a portion of the tissue gripping member and a portion of the flexible member (e.g., an arm portion such as arm 206 of the embodiment of FIGS. 10A-OC) as illustrated in the exemplary embodiment of FIGS. 10A-10C. The suture lines may be formed into loops or may be threaded or wrapped around the tissue gripping member and the arm (or other portion of the flexible member) before being tightened and/or tied off in order to secure the tissue gripping member to the flexible member.

In some embodiments, the tissue gripping member and/or the flexible member may include holes, and the one or more suture lines may be passed through one or more of the holes in order to fasten or further secure the tissue gripping member to the flexible member. For example, as shown by the embodiment illustrated in FIGS. 10A-10C, the tissue gripping member may have a plurality of holes, with each hole configured to correspond to a hole on an arm of the flexible member when the tissue gripping member is properly positioned near or against the arm of the flexible member. One or more suture lines may pass through one or more pairs of corresponding holes as it is laced, wrapped, looped, or threaded around the tissue gripping member and the arm.

In some embodiments, one or more suture lines may also be passed through or lodged within a slotted recess of the tissue gripping member as it is laced, wrapped, looped, or threaded around the tissue gripping member and the arm. In such embodiments, the slotted recesses may further aid in securing the suture line in place and/or in preventing loosening, slippage or other unwanted movement of the suture line.

Additionally, or alternatively, the tissue gripping member may be secured to or further secured to the flexible member by adding a cover to the tissue gripping device that inserts over the arm of the flexible member and over the tissue gripping member (or portions of such) in order to hold the tissue gripping member in place against the flexible member.

For example, in some embodiments (such as in the embodiment illustrated in FIGS. 11A-11C), the cover may be a polymer material coated onto or otherwise applied to the tissue gripping device (or portions thereof). The polymer coating may then be allowed to set, cure, or otherwise form into a cover that holds the tissue gripping member in place against the arm of the flexible member. Additionally, or alternatively, the polymer coating may act as an adhesive, and may be applied to the mating surface and/or attachment surface to adhere the surfaces together.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A gripping assembly for a fixation device, the gripping assembly comprising:

a flexible member comprising an arm having an attachment surface;

a tissue gripping member comprising:

a mating surface engaged to the attachment surface of the arm, a tissue gripping surface configured to engage native tissue, and a plurality of frictional elements configured to resist movement of the native tissue relative the tissue gripping surface; and a first cover positioned over at least a portion of the arm and over at least a portion of the tissue gripping member to couple the tissue gripping member to the arm, the first cover acting as an adhesive applied to at least one of the mating surface or the attachment surface to adhere the tissue gripping member to the arm as the mating surface is positioned against the attachment surface.

2. The gripping assembly of claim 1, wherein the first cover is a polymer cover.

3. The gripping assembly of claim 2, wherein the polymer cover is formed on least a portion of the tissue gripping member and at least a portion of the flexible member by dipping, spraying, coating or adhering.

4. The gripping assembly of claim 2, wherein the polymer cover is applied to the tissue gripping member and the arm while the tissue gripping member is held in place against the flexible member.

5. The gripping assembly of claim 1, wherein the first cover is formed in whole or in part of polyethylene, terephthalate, polyester, cotton, polyurethane, expanded polytetrafluoroethylene, silicon, biocompatible polymers, or fibers.

6. The gripping assembly of claim 5, wherein the first cover is formed by fabric, mesh, textured weave, felt, looped or porous structure.

7. The gripping assembly of claim 6, wherein the first cover is impregnated or coated with drugs, antibiotics, anti-thrombosis agents, or anti-platelet agents.

8. The gripping assembly of claim 1, wherein the first cover is configured with the plurality of frictional elements exposed.

9. The gripping assembly of claim 1, wherein the first cover is positioned over an entirety of the tissue gripping member and a portion of the arm adjacent to the tissue gripping member.

10. The gripping assembly of claim 1, wherein the first cover is configured with a portion of the tissue gripping member exposed.

11. The gripping assembly of claim 1, wherein the flexible member comprises a second arm, and further wherein a second tissue gripping member is coupled to the second arm of the flexible member by a second cover.

12. The gripping assembly of claim 1, further comprising one or more sutures further coupling the tissue gripping member to the arm.

13. The gripping assembly of claim 12, wherein the tissue gripping member and the arm each include one or more holes, and the one or more sutures form one or more loops extending through the holes of the tissue gripping member and the arm.

14. A gripping assembly for a fixation device, the gripping assembly comprising:

a bend feature;

an arm extending from the bend feature and being configured to move about the bend feature between a relaxed state and a stressed state, the arm having a first side and a second side opposite the first side, the second side having an attachment surface;

a tissue gripping member having a first side and a second side opposite the first side, the first side having a mating surface engaged to the attachment surface, and the second side having a plurality of frictional elements extending therefrom; and a cover conforming to and extending over at least a portion of the first side of the arm and over at least a portion of the second side of the tissue gripping member so as to hold the attachment surface of the tissue gripping member in engagement with the mating surface of the arm, wherein the cover is the only structure that maintains the attachment surface in engagement with the mating surface.

15. The gripping assembly of claim 14, wherein the cover is a polymer cover.

16. The gripping assembly of claim 15, wherein the cover is at least one of polyethylene terephthalate, polyester, polyurethane, and expanded polytetrafluorethylene (ePTFE).

17. The gripping assembly of claim 15, wherein the cover is formed on the arm and the gripping member by one of dipping, spraying, coating, or adhering.

18. The gripping assembly of claim 14, wherein the plurality of frictional elements extend through the cover.

19. A fixation device for securing tissue comprising:

a distal element moveable between an open position and a closed position; and a proximal element disposed opposite the distal element and having an arm and a tissue gripping member, the arm having an attachment surface, and the tissue gripping member having a mating surface engaged to the attachment surface of the arm and a plurality of frictional elements extending from the tissue gripping member in a direction toward the distal element; and a cover extending over at least a portion of the arm and at least a portion of the tissue gripping member so as to hold the tissue gripping member in place against the arm, the tissue gripping member being held in engagement with the arm solely by the cover, wherein the tissue gripping member is disposed between the distal element and the arm.

* * * * *